US010557778B2

(12) United States Patent
Seibel et al.

(10) Patent No.: US 10,557,778 B2
(45) Date of Patent: Feb. 11, 2020

(54) OPTICAL PROJECTION TOMOGRAPHY MICROSCOPY (OPTM) FOR LARGE SPECIMEN SIZES

(71) Applicants: Eric J. Seibel, Seattle, WA (US); Qin Miao, Seattle, WA (US); Ryan Lee Coe, Seattle, WA (US); Per G. Reinhall, Seattle, WA (US)

(72) Inventors: Eric J. Seibel, Seattle, WA (US); Qin Miao, Seattle, WA (US); Ryan Lee Coe, Seattle, WA (US); Per G. Reinhall, Seattle, WA (US)

( * ) Notice: Subject to any disclaimer, the term of this patent is extended or adjusted under 35 U.S.C. 154(b) by 802 days.

(21) Appl. No.: 14/453,938

(22) Filed: Aug. 7, 2014

(65) Prior Publication Data

US 2014/0342395 A1 Nov. 20, 2014

Related U.S. Application Data

(62) Division of application No. 13/091,088, filed on Apr. 20, 2011, now Pat. No. 8,867,803.

(60) Provisional application No. 61/326,073, filed on Apr. 20, 2010.

(51) Int. Cl.
*G01N 1/30* (2006.01)

(52) U.S. Cl.
CPC ...................... *G01N 1/30* (2013.01)

(58) Field of Classification Search
CPC ........................................ G01N 1/30
USPC ............................................ 435/30
See application file for complete search history.

(56) References Cited

U.S. PATENT DOCUMENTS

| 5,197,484 | A | 3/1993 | Kornberg et al. |
| 5,427,742 | A | 6/1995 | Holland |
| 5,680,484 | A | 10/1997 | Ohyama et al. |
| 5,980,469 | A | 11/1999 | Burbank et al. |
| 6,472,216 | B1 * | 10/2002 | Chiang .................. G01N 1/30 |
| | | | 252/408.1 |
| 7,156,814 | B1 | 1/2007 | Williamson, IV et al. |
| 7,197,355 | B2 | 3/2007 | Nelson |
| 7,218,393 | B2 | 5/2007 | Sharpe et al. |
| 7,338,760 | B2 | 3/2008 | Gong et al. |
| 7,572,236 | B2 | 8/2009 | Quick et al. |
| 7,738,945 | B2 | 6/2010 | Fauver et al. |
| 7,806,835 | B2 | 10/2010 | Hibner et al. |
| 8,143,600 | B2 | 3/2012 | Seibel et al. |
| 8,152,738 | B2 | 4/2012 | Li et al. |
| 8,267,868 | B2 | 9/2012 | Taylor et al. |
| 8,329,120 | B2 | 12/2012 | Williamson, IV et al. |
| 8,404,229 | B2 | 3/2013 | Fraser et al. |
| 8,529,468 | B2 | 9/2013 | Hoffa et al. |
| 8,673,645 | B2 | 3/2014 | Quake et al. |
| 2003/0082568 | A1 | 5/2003 | Phan et al. |
| 2003/0119176 | A1 * | 6/2003 | Krulevitch ........... A61B 5/0084 |
| | | | 435/287.2 |
| 2003/0194716 | A1 | 10/2003 | Knoll |
| 2005/0085721 | A1 * | 4/2005 | Fauver ................. G02B 21/002 |
| | | | 600/425 |
| 2006/0252054 | A1 | 11/2006 | Lin et al. |
| 2007/0077547 | A1 | 4/2007 | Shvets et al. |
| 2009/0125242 | A1 * | 5/2009 | Choi ...................... G01N 21/45 |
| | | | 702/19 |
| 2010/0055673 | A1 * | 3/2010 | Agarwal ........... B01L 3/502707 |
| | | | 435/5 |

OTHER PUBLICATIONS

"Engineering of Tissue Optical Properties | Microvascular Therapeutics and Imaging Laboratory," http://choi.bli.uci.edu/, accessed Apr. 15, 2011, now attached as http://choi.bli.uci.edu/research/optical-clearing, accessed Mar. 24, 2014, 1 page.
"Micronics Microfluidics: Lab Automation & Nanotechnology," retrieved from http://www.micronics.net/technology, accessed Feb. 27, 2014, 1 page.
"PY Current Research Projects," retrieved from http://faculty.washington.edu/yagerp/pyresearchcurrent.html, accessed Feb. 27, 2014, 3 pages.
Botcherby et al., "Real-time extended depth of field microscopy," *Optics Express* 16(26:21843-21848, Dec. 22, 2008.
Fauver et al., "Three-dimensional imaging of single isolated cell nuclei using optical projection tomography," *Optics Express* 13(11):4210-4223, May 30, 2005.
Herrera et al., "Indirect Methods of Collocation: Trefftz-Herrera Collocation," *Numerical Methods for Partial Differential Equations* 15(6):709-738, Nov. 1999.
Hine, "Block Staining of Mammalian Tissues With Hematoxylin and Eosin," *Stain Technology* 56(2):119-124, 1981.
Jenssen et al., "Endoscopic ultrasound-guided fine-needle aspiration biopsy and trucut biopsy in gastroenterology—An overview," *Best Practice & Research Clinical Gastroenterology* 23:743-759, 2009.
Kim et al., "Breast Cancer Diagnosis Using a Microfluidic Multiplexed Immunohistochemistry Platform," *PLoS One* 5(5), 12 pages, May 2010.
Miao et al., "Resolution improvement in optical projection tomography by the focal scanning method," *Optics Letters* 35(20):3363-3365, Oct. 15, 2010.
Resnikoff and Wells, *Wavelet Analysis: The Scalable Structure of Information*, Springer-Verlag, New York, 1998, Chapter 10, "Wavelet Calculus and Connection Coefficients," and Chapter 11, "Multiscale Representation of Geometry," pp. 236-273. (27 total pages).

(Continued)

*Primary Examiner* — Nghi V Nguyen
(74) *Attorney, Agent, or Firm* — Seed IP Law Group LLP

(57) ABSTRACT

An imaging and diagnostic system and method for focal scanning of a specimen using optical projection tomographic microscopy and computer generation of three-dimensional images is disclosed. One embodiment includes a light source and an imaging system having an adjustable focal position, which acquires a plurality of digital 2D projection images of biological tissue placed within a specimen tube that translates and rotates past an optical lens in a helical pattern. A computer captures the images and generates a 3D composite image. Also disclosed is a system and method for preparing a specimen for optical microscopy. One embodiment includes fixing, staining, and/or optically clearing biological tissue within a microfluidic specimen chamber prior to placement in a specimen tube.

24 Claims, 37 Drawing Sheets

(56) References Cited

OTHER PUBLICATIONS

Sharpe et al., "Optical Projection Tomography as a Tool for 3D Microscopy and Gene Expression Studies," *Science 296*:541-545, Apr. 19, 2002.
Duong et al., "Influence of refrigerated storage on tensile mechanical properties of porcine liver and spleen," *International Biomechanics* 2(1):79-88, 2015. (11 pages).
Kemper et al., "Biomechanical Response of Human Liver in Tensile Loading," *Annals of advances in automotive medicine 54*:15-26, 2010.
Untaroiu et al., "Modeling the biomechanical and injury response of human liver parenchyma under tensile loading," *Journal of the Mechanical Behavior of Biomedical Materials 41*:280-291, 2015.
Wu et al., "Bone and Soft-Tissue Lesions: What Factors Affect Diagnostic Yield of Image-guided Core-Needle Biopsy?" *Radiology 248*(3):962-970, 2008.

\* cited by examiner

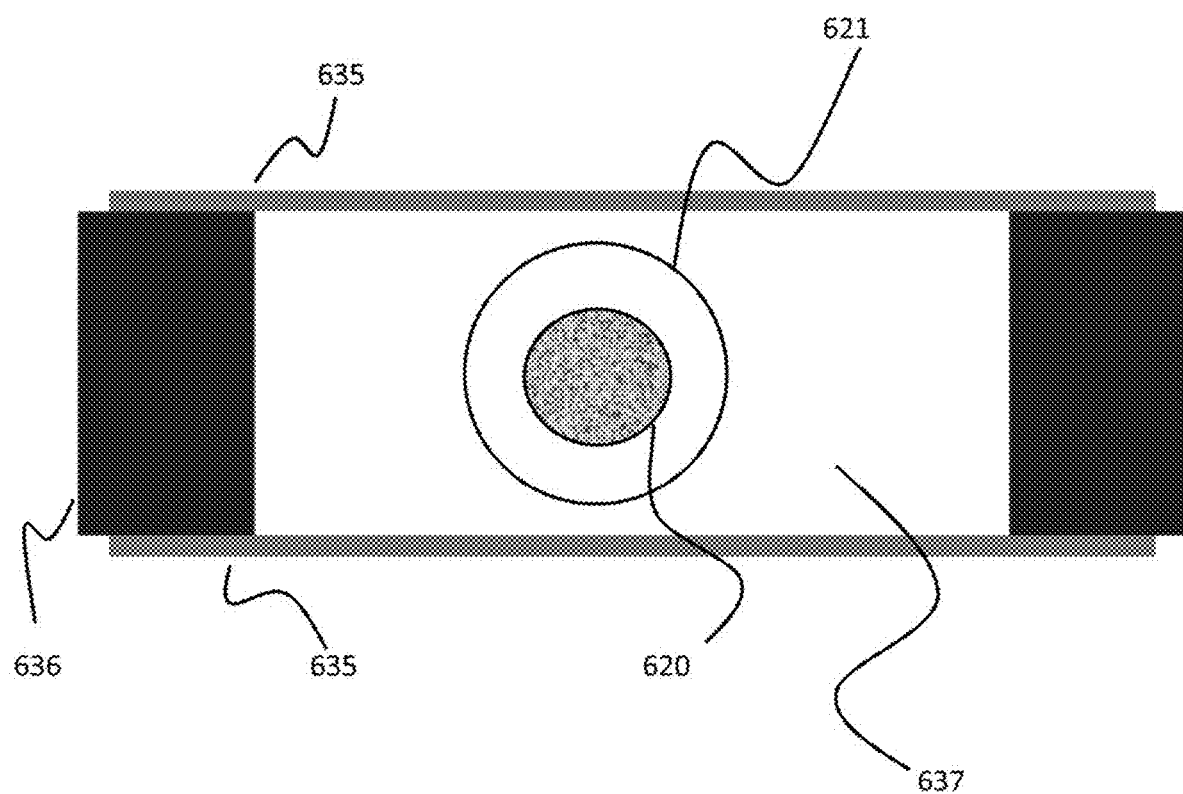

OPTICAL PROJECTION TOMOGRAPHY MICROSCOPY (OPTM) FOR LARGE SPECIMEN SIZES

RELATED APPLICATIONS

This application is a divisional application of U.S. patent application Ser. No. 13/091,088, filed Apr. 20, 2011, which claims the benefit of the filing date under 35 U.S.C. § 119(e) of Provisional U.S. Patent Application Ser. No. 61/326,073, filed Apr. 20, 2010. This application hereby incorporates by reference the U.S. priority applications enumerated herein.

BACKGROUND

Technical Field Text

Diagnosis of disease is made by matching current observations to established correlations of past observations to the known clinical outcomes. For a disease such as cancer, clinical diagnosis is most often made by taking a sampling of cells or tissues from an organ or region of the body and examining the specimen using an optical microscope. Many observations are made, such as the tissue structure, cell morphology, and subcellular morphology and chromatin distribution in the nucleus. To obtain samples of the cells and/or tissue, a biopsy is often taken.

There are many different ways to take a biopsy specimen. Open surgical techniques allow direct access to tissue so specimen size does not have to be limited. Minimally invasive techniques impart less trauma to the healthy tissues of the body, but specimen size per biopsy is usually limited. Minimally invasive biopsy tools for tissue sampling range from surgical cuttings and punches, forceps, and coring needles. Less invasive and typically smaller biopsy tools are used for cell sampling, which include fine-needle aspiration, brushing, and tissue washes.

Tissue biopsy is generally preferred over cell biopsy because tissue architecture is preserved in the tissue biopsies. Although disease diagnosis such as cancer can be made with individual cells, the tissue architecture provides additional information about the location and extent of the disease. The invasiveness of cancer can be determined from tissue biopsy rather than cell biopsy, which affects the treatment of the patient.

Needle biopsy can take either cells or tissue. The largest needles have sharp tips that pierce the tissue and then side chambers that cut the tissue pressing against the needle shank. These side-cutting needles are used to take 1-4 mm diameter cores of tissue, which are often a couple centimeters long. Needles that have cutting tips can also take a core of tissue. These forward-cutting needles can be smaller in diameter, but below 0.5 mm inner diameter, the needle is not able to reliably remove the core specimen from the body. Thus, core needles are typically larger than 0.5 mm inner diameter.

Once a core of tissue is taken from the body, the specimen is handled in similar fashion to all tissues removed for disease diagnosis. The tissue is chemically fixed and stained with absorptive dyes. Typically hematoxylin stain is used to make the nuclear structure blue in color, while eosin is used to stain the cytoplasmic structure pink. To observe the stained tissue structure at sufficient spatial resolution, an optical microscope is used in transmission. However, tissue attenuates transmittance of white light, primarily due to scattering from refractive index differences of the structures in the tissue. Since the optical microscope is limited to tissue thicknesses of less than 0.1 mm, thin sections of the biopsy specimen are cut in an orderly fashion to represent the three-dimensional (3D) tissue architecture from the two-dimensional (2D) images.

Thinner needles are less invasive, but are not used to reliably acquire a tissue specimen. The thin needle is used to acquire cells dislodged and disassociated from the tissue. The biopsy of aspirated cells from these thin needles is called a fine needle aspirate (FNA). The FNA specimen is most often analyzed cytologically, as individual cells spread on an optical microscope glass slide and observed at higher optical magnification than tissue specimens. Often the exact same types of absorptive stains are used to color the cell components. However, a different chemical fixative is often used in cytology, which better preserves the chromatin structure.

In summary, the smaller and less invasive needles acquire FNA specimens, which consist of isolated cells in a slurry, while larger needles are used to acquire core tissue specimens. Between these needle sizes, core tissue specimens are acquired occasionally. For example, needles of 22-gauge or 0.4 mm inner diameter can acquire core specimens in approximately 3 out of four cases, as reported by C. Jenssen and C. F. Dietrich (2009) "Endoscopic ultrasound-guided fine-needle aspiration biopsy and trucut biopsy in gastroenterology—an overview," Best Practice & Research Clinical Gastroenterology, 23: 743-759. The sizes of biopsy needles are listed by gauge, which is converted to inner diameter in millimeters below.

| Inner diameters of needles and their medical use | | |
|---|---|---|
| Gauge (G) | Inner diameter (ID) mm | Medical use |
| 11 | 2.4 | core |
| 14 | 1.6 | core |
| 16 | 1.2 | core |
| 19 | 0.7 | core |
| 21 | 0.5 | core/FNA |
| 22 | 0.4 | FNA |
| 25 | 0.2 | FNA |

In the above example of endoscopic ultrasound-guided FNA biopsy, the advantage of the thinner needle is two-fold. (1) The smaller needle can be fit more easily through the working channel of a flexible endoscope that reaches the pancreas by passing through the mouth, throat, and stomach. Thus, the endoscope must have tight curves that restrict larger-sized needle devices from reaching all regions of the pancreas. For example, only the thinner needle devices, such as FNA, can be used to biopsy from all regions of the pancreas using conventional flexible endoscopes. The FNA needles are typically 5× thinner than the standard core needle. (2) The smaller needle is less invasive, which is much more important for delicate organs such as the pancreas, as pancreatitis is life threatening. Thinner needles are very useful in other organs like the brain.

However, the advantage of the core needle biopsy is the more valuable tissue specimen. Tissue specimens are preferred for being able to better determine the extent and invasiveness of disease, such as cancer.

Thin Needle Core Biopsy (TNCB)

Even though engineering improvements in thin-needle coring devices can produce finer core specimens, such as 0.25 mm in diameter, the pathologist has no established procedure to make a diagnosis from a less invasive tissue biopsy. A thin-needle core biopsy (TNCB) of 0.25 mm diameter by one to two centimeters in length is too small and fragile of a tissue specimen to handle. The cell-to-cell bonds holding together diseased tissue such as cancer are often much weaker than normal tissue. Manual techniques used for the conventional core needle biopsy specimens of roughly 5× to 10× diameter cannot be used without damaging the tissue structure. Any TNCB specimen that is sub-millimeter in diameter is expected to be too small for the traditional method of cutting thin slices in an orderly fashion to determine extent and invasiveness of disease.

Although TNCB specimens that are sub-millimeter in diameter are considered too small mechanically, these same specimens are considered too thick to make a straightforward optical diagnosis. Because white-light light transmission through tissue is usually limited by optical scattering to less than 0.1 mm, TNCB specimens greater than this diameter cannot be imaged directly on a conventional microscope used by pathologists. Thus, TNCB specimens in the range of 0.1 to 1 mm in diameter are problematic for making disease diagnosis, considered too small for conventional sample handling and preparation, while also considered too large for routine optical imaging for making a diagnosis. Thus new techniques in both specimen preparation and imaging are necessary to use the lease invasive tissue biopsy sample for disease diagnosis.

Advanced methods for small-sized sample preparation are still inadequate. More automated devices for acquiring core biopsy specimens from a needle has been proposed which can reduce manual handling requirements. For example, a core needle biopsy device has been proposed that has a specimen collection and retention chamber where the specimen can have applied fluid and vacuum for processing the specimen by Quick et al., (2009) in U.S. Pat. No. 7,572,236, entitled, "BIOPSY DEVICE WITH FLUID DELIVERY TO TISSUE SPECIMENS." However, human handling is still required for histological imaging since there is no mechanism for further specimen handling before diagnostic imaging.

Automated cell handling and in vitro diagnostics have been proposed for isolated cells and sub-cellular constituents, but there has been little advancement using this technology for larger multicellular specimens like TNCB. The first use of a microfluidic system for human biopsy tissue samples for histopathological diagnosis used a large tissue slice where smaller microfluidic chambers were placed on top of the tissue, see Kim et al., (May 2010) in PLoS ONE online journal (volume 5, issue 5, e10441), entitled, "Breast cancer diagnosis using a microfluidic multiplexed immunohistochemistry platform." The resulting diagnosis by optical imaging was made from these individual small chambers that provided diagnostic sampling from the single large tissue specimen. Biopsy specimens, such as TNCB, are not inserted into a microfluidics device for automated specimen preparation and diagnosis for the entire biopsy specimen.

Microfluidics was first developed in the 1980s as a means for precisely manipulating fluids. The field has been expanded significantly to biological applications through major university research, such as Yager Lab at the University of Washington (http://faculty.washington.edu/yagerp/, accessed 19 Apr. 2011) and even spread to industrial applications at companies such as Micronics (http://www.micronics.net/, accessed 19 Apr. 2011).

Techniques for optical imaging biopsy specimens are inadequate for TNCB specimens. Typically biopsies from thin needles of <0.1 mm are generated into a slurry of cells, such as aspirates (e.g. FNA). These specimens have lost most or all of their cell-to-cell bonds and tissue architecture is lost. The methods employed to image these isolated cells and tissue fragments consist of near monolayers of cells to smears of cells on a microscope slide for standard image analysis by a cytologist. These cell samples can also be analyzed using flow cytometers, imaging flow cytometers, and the optical projection tomography microscope, see Fauver et al., (2005) "Three-dimensional imaging of a single isolated cell nucleus using optical projection tomography," Optics Express 13(11): 4210-4223.

Tissue biopsies that are larger have a wider array of techniques used for optical imaging, although over 90% of all cancer diagnosis is performed using thin sections of tissue that is stained for conventional bright field optical imaging using white-light in transmission. The more advanced techniques for optical imaging are moving optical diagnosis from reliance on 2D images to more three-dimensional images. These techniques range from laser scanning confocal, multiphoton excitation, to new super-resolution optical imaging. However all these techniques rely on fluorescence marking of tissue structures. Thus there is a gap between these research microscopes and clinical diagnosis which relies not on fluorescence, but on absorptive stains that are imaged with white light that is transmitted through the tissue.

Alternative imaging techniques such as optical coherent tomography (OCT), holographic imaging, and enhanced backscattering techniques rely not on the absorption of light from stained tissue structures, but on the scattering of light from unlabeled structures. Because there is no correlation of these clinical outcomes to new microscopic images of tissue and cells, there is no basis for making routine clinical diagnosis of disease. This same problem holds for new optical techniques that use chemical signatures of cell and extracellular structures to form images, such as coherent Raman scattering.

A technique that has produced 3D images of tissue that has direct clinical relevance is from Sharpe et al. (2002) "Optical projection tomography as a tool for 3D microscopy and gene expression studies," Science 296, 541-545. Optical projection tomography (OPT) uses a narrow beam of light that has a large depth of focus, which is on the length scale of the tissue specimen thickness. This beam of light is scanned through the tissue as the tissue orientation is changed (i.e., specimen is rotated). The resulting series of optical projection images are created in transmission so standard absorptive stains of hematoxylin and eosin can be used. The series of 2D images can be used to create a 2D image using a 3D reconstruction mathematical technique that is similar to x-ray computed tomography.

Advantages of 3D Imaging for Disease Diagnosis

Imaging tissue in 3D is advantageous over one or more images in 2D for several reasons. The original object of cells and tissue are three-dimensional and the human brain is trained to interpret 3D objects in their natural state. A 3D image and 3D visualization can provide clear localization of the disease and surrounding tissue without ambiguity from overlapping structures. The extent of disease can be clearly assessed and regions of interest measured. Invasiveness of the suspected disease can be tracked through the surrounding tissue. Surgery and treatment regimens can be better planned for the patient. The advent of 3D computed tomography (CT) using x-rays has replaced standard 2D x-rays for many medical applications due to these reasons.

For the case of TNCB specimens, there are advantages to imaging in 3D rather than 2D. The advantage of imaging tissue rather than dissociated cells is that more than simply the presence of disease, such as cancer, can be made from the tissue specimen. The location of the cancer cells or tumor, extent of disease, and most importantly the invasiveness of cancer can be ascertained. For example, determining if cancer has migrated from the epithelium through the basement membrane to the capillary beds is extremely important information for treating the patient and managing the disease.

The advantage of 3D imaging the entire TNCB specimen is that there are no sampling errors. Unlike conventional core needle biopsies of 1 to 3 mm in diameter, the entire specimen is too large to optically image the entire specimen, so thin slices must be taken at different locations. There is risk of missing small tumors and especially early cancers. Since the TNCB specimens of 0.1 to 1 mm are smaller they can be optically imaged in their entirety in 3D. Again, 2D imaging would take only a cross-sectional sampling of the 3D specimen, although this is currently the standard clinical practice.

3D imaging of biological specimens has been accomplished in the transmission mode, which allows the use of clinically important absorptive stains. Two similar techniques of Ohyama et al., (1997) in U.S. Pat. No. 5,680,484 entitled, "OPTICAL IMAGE RECONSTRUCTING APPARATUS CAPABLE OF RECONSTRUCTING OPTICAL THREE-DIMENSIONAL IMAGE HAVING EXCELLENT RESOLUTION AND S/N RATIO," and Nelson (2007) in U.S. Pat. No. 7,197,355 entitled, "VARIABLE-MOTION OPTICAL TOMOGRAPHY OF SMALL OBJECTS," never disclose a means for forming a continuous image of a tissue specimen along the longitudinal axis of the rotating tube. Whereas, Sharpe & Perry (2007) in U.S. Pat. No. 7,218,393 entitled, "ROTARY STAGE FOR IMAGING A SPECIMEN," imaged a single specimen using a focused beam of light through the rotating specimen within a stationary chamber with sidewalls that are orthogonal to the optical axis. The main shortcoming of this OPT technique is the low spatial resolution which is defined by the size of this focused beam of light, see Miao et al., (2010) "Resolution improvement in optical projection tomography by the focal scanning method" Optics Letters 35(20): 3363-3365. In addition, there is a problem with this technique for rotating long, thin, and fragile tissue specimens to form 3D images since no transparent containment tube is used.

BRIEF SUMMARY

The invention is a system and method for creating an image for diagnosing a tissue biopsy specimen taken with a thin needle while the specimen is continuously retained in a single channel structure. This thin-needle core biopsy (TNCB) has a typical size of 0.05 mm to 1.5 mm in outer diameter and 5 mm to 40 mm in length and is cylindrical in shape. The system consists of a microfluidic device that accepts a TNCB specimen, which provides chemical processing and optical inspection for diagnostic imaging using the Optical Projection Tomography Microscopy (OPTM) technique for large specimen sizes. The microfluidics device performs at least one function of, washing, fixing, staining, clearing (optically), and embedding of the tissue in polymer or other medium. The processed TNCB is loaded into a tube and a single continuous image is generated of the specimen using OPTM. The OPTM instrument is used to acquire a series of images of the specimen and construct at least one diagnostic image. Image generation can involve image stitching and blending a series of images in 3D or by 3D image reconstruction. Standard image processing and enhancement techniques such as digital filtering and deblurring (e.g. deconvolution) may also be applied during this process.

BRIEF DESCRIPTION OF THE DRAWINGS

FIG. 11B schematically shows OPTM stage containing the TNCB specimen within the transparent tube which is immersed within a refractive index matching medium (axial side view).

DETAILED DESCRIPTION OF THE DRAWINGS AND THE PRESENTLY PREFERRED EMBODIMENTS

Figure 1A:
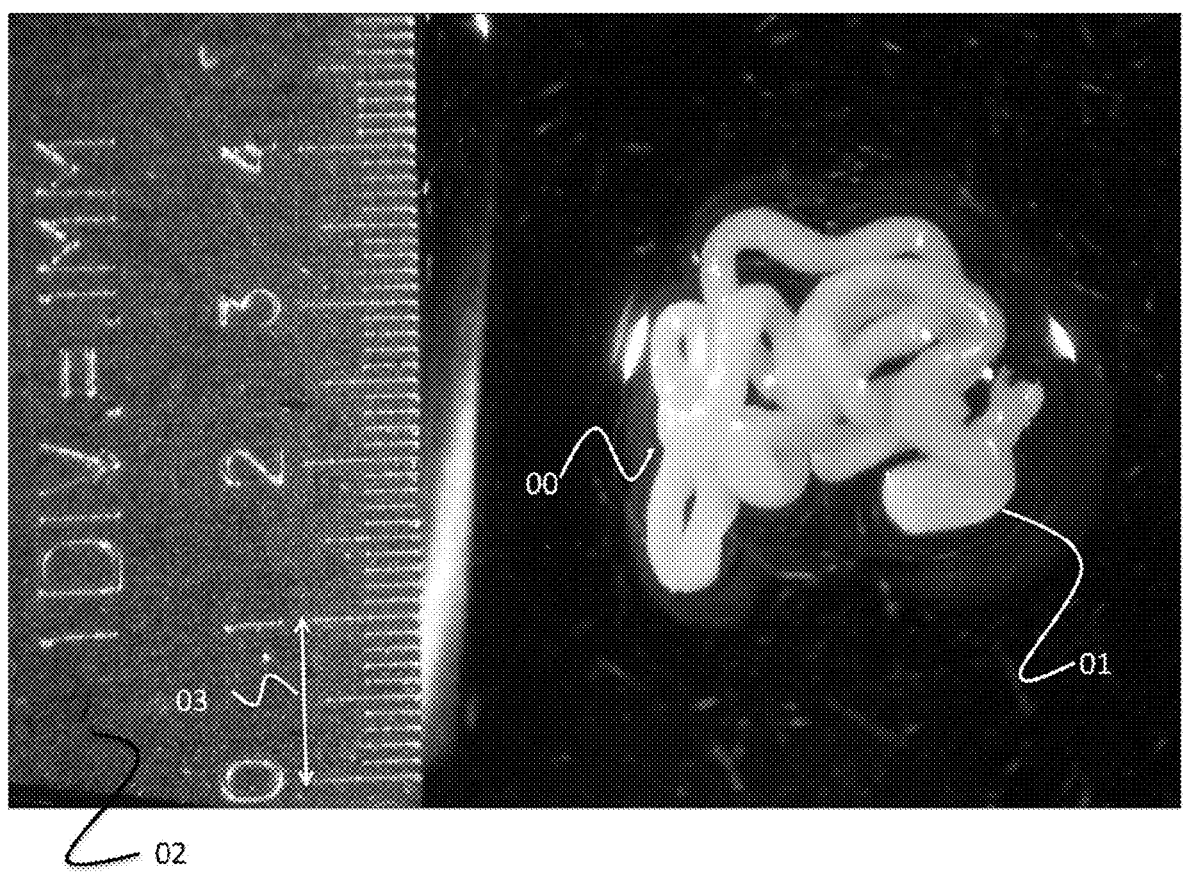
FIG. 1A Photograph of curled TNCB specimen that is 0.25 mm in diameter and over 20 mm in length, FIG. 1B Photograph of same specimen in (A) that is made translucent by applying an optical clearing solvent of pure methyl salicylate, FIG. 1C Series of photographs of skin that is reversibly cleared by applying glycerol, then saline, and FIG. 1D Photograph of a straight TNCB specimen that is 0.25 mm in diameter and approximately 14 mm in length.

FIG. 1A shows a photograph TNCB specimen 00 cut from fresh chicken liver using a forward cutting thin needle with 0.25 mm inner diameter. Upon pushing out the biopsy specimen with a metal rod that fills the needle lumen, the tissue was expelled and naturally curled. Specimen 00 retained the same diameter as the needle ID (0.25 mm) and is slightly longer than 20 mm. Specimen 00 is photographed in a drop of fixative 01 (50% isopropyl alcohol) by scale bar 02 having numbered markings of millimeter increments. The length of 03 is 1 millimeter. The white color of specimen 00 illustrates the high degree of optical scattering when illuminated with white light. This strong light scattering in tissue specimen 00 causes low contrast, spatial resolution, and imaging depth of cells below the tissue surface. This scattering is predominantly the result of mismatches between the cell membrane (refractive index around 1.5) and the intracellular and extracellular tissue fluids (refractive index around 1.3). One method that reduces optical scattering is by the optical immersion method, which reduces the difference between refractive index within the tissue by exchanging the tissue fluids with an optical clearing solution of high refractive index (e.g. methyl salicylate of 1.53 or benzyl-alcohol benzyl-benzoate, BABB, of 1.55) to match the refractive index of the cell membranes. When the specimen is soaked in optical clearing solution the white color almost disappears and the specimen becomes nearly translucent.

Figure 1B:
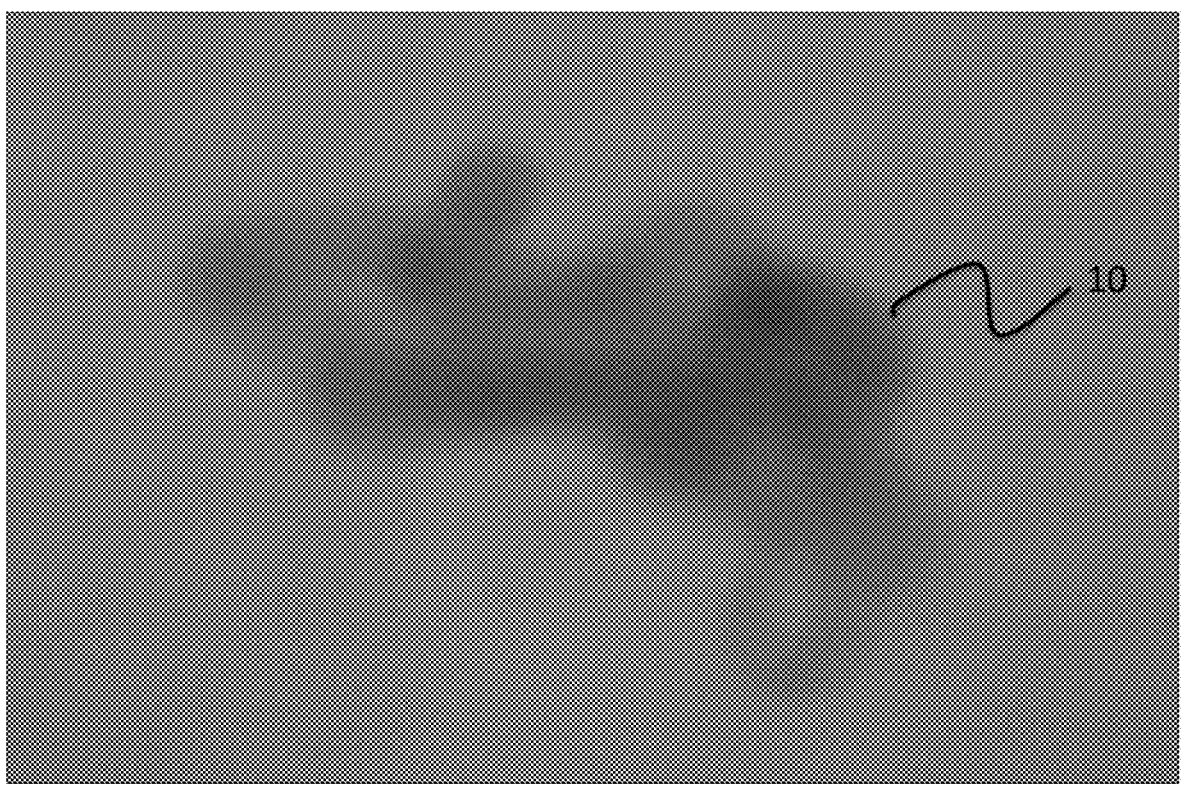
Figure 1C:
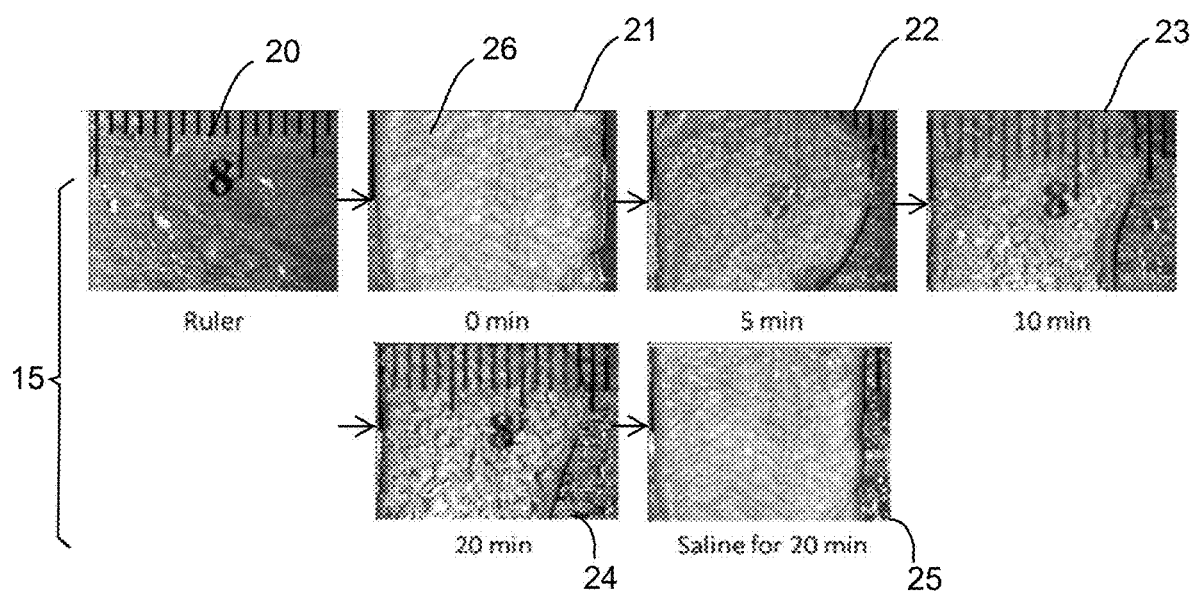

FIG. 1B is a photograph of the same TNCB specimen 10 from FIG. 1A shown after TNCB specimen 00 is immersed in optical clearing agent, pure methyl salicylate. Specimen 10 is translucent due to a reduction in optical scattering. Natural tissue contrast from optical absorption can now be seen from the blood, as the specimen no longer looks white but translucent pink with visible light illumination. Because the tissue specimen was in an aqueous environment, the specimen was first immersed in a succession of graded ethanol/water mixes until pure ethanol, since optical clearing agent is not miscible in water, but with ethanol. To achieve tissue immersion in pure methyl salicylate, the specimen was immersed in a succession of graded ethanol/methyl salicylate until finally in pure methyl salicylate. To more clearly demonstrate this optical clearing effect of increase in transmittance of white-light of approximately 15× depending on type of tissue, clearing, agent, and optical frequency, a time-series of photographs is illustrative. FIG. 1C is a series 15 of photographs that illustrate the optical clearing of 0.5 mm thick skin using glycerol as the optical clearing agent, which is reversible with saline, (http://choi.bli.uci.edu/, accessed 15 Apr. 2011). Ruler 20 is used as a scale bar. Skin 26 is immersed in glycerol and taken out for imaging at 0, 5, 10, 20 minutes after immersion. Skin 26 is seen to be more and more transparent as shown in images 21, 22, 23, and 24. Then cleared skin 26 in image 24 is immersed in saline and skin 26 becomes opaque again, which is shown in image 25.

Figure 1D:
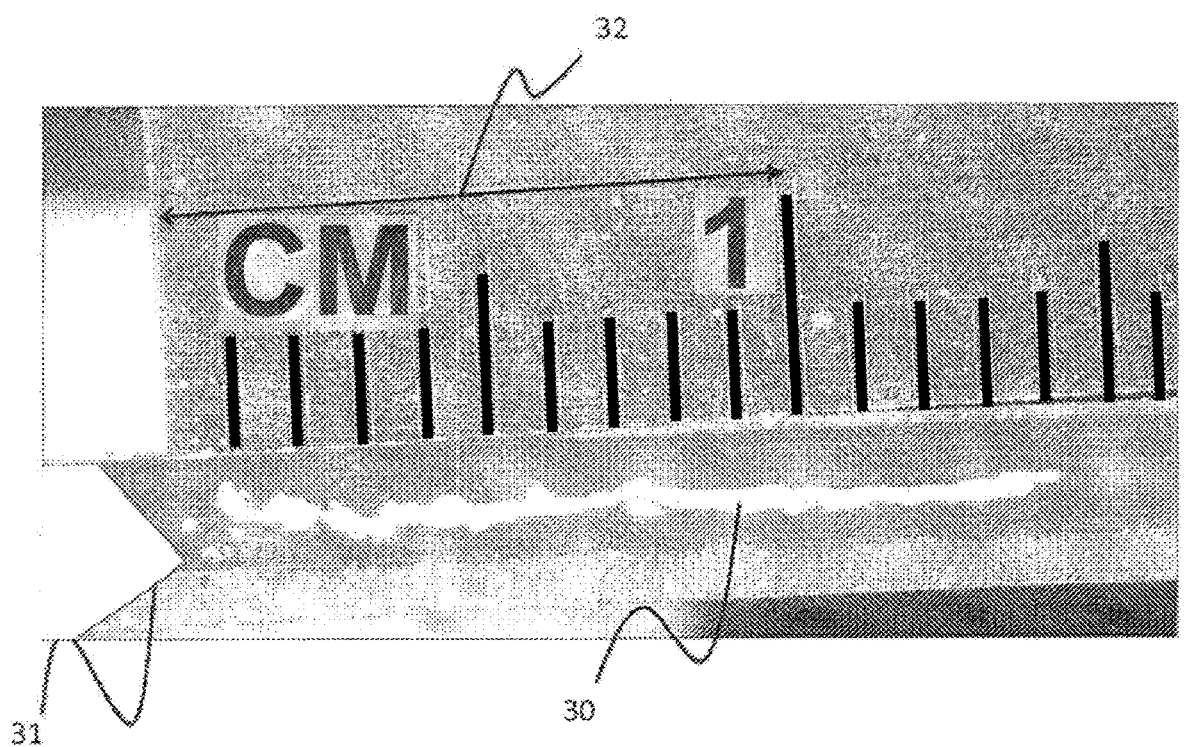

FIG. 1D shows a photograph of another 0.25 mm diameter TNCB specimen 30 that was acquired in the same method as described for FIG. 1A. However, during expulsion from the needle with a metal plunger, the needle tip was moved along the vertex of a V-groove 31. Resulting TNCB specimen 30 could be laid relatively straight. The specimen is photographed in a drop of the fixative (50% isopropyl alcohol) by scale bar 32, which represents 10 millimeters. Specimen 30 is measured to be about 14 mm. However, these long and TNCB tissue specimens are fragile structures and must be handled delicately or they will deform and fragment. The original tissue structure may be well preserved if the TNCB specimen constantly remains in a channel structure that replicates the original coring needle, such as a microfluidics channel of similar size.

Figure 2A:
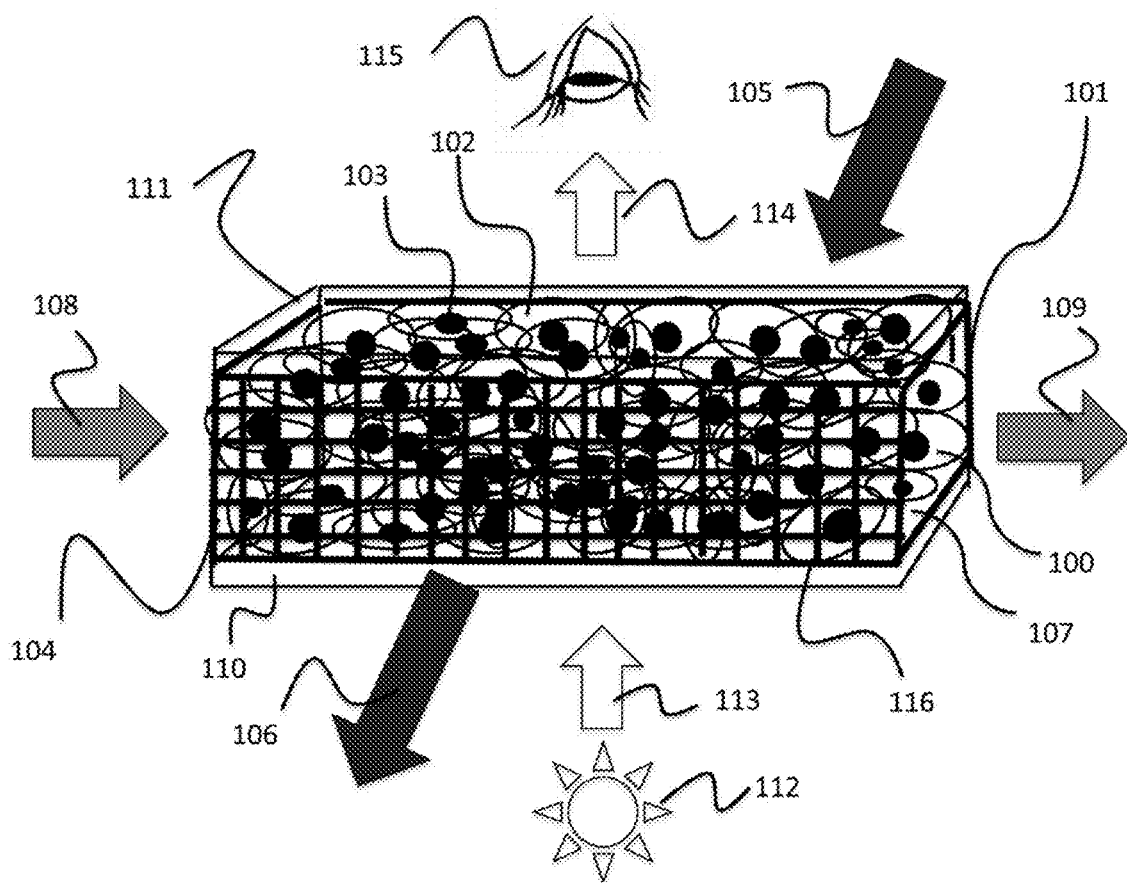
FIG. 2A schematically shows a segment of a tissue specimen filling the inner part of a microfluidic chamber that will be axially moved in and out of the chamber, and undergo a series of fluid washes for chemical exchanges for the purpose of preparing the specimen for optical imaging in transmission.

FIG. 2A shows schematically an example of a specimen axial segment 100 that is held within a section of rectangular microfluidics chamber 101 for sample preparation. Although in this illustration, tissue specimen segment 100 is a schematic of a TNCB tissue segment composed of oval cells 102 with single nucleus 103, specimen can also be whole organ, live specimen or engineered tissue Biological tissue is defined as any small multi-cellular organism, or sample from a multi-cellular organism or any fragment thereof. The near and far sides of the channel are composed of screen interface 104 that can pass fluids passing through the specimen, chamber with open screen mesh as illustrated by near and far arrows 105 and 106, while retaining the specimen integrity and cellular constituents of tissue. The screen can be of many different configurations, such as the cross-hashed meshwork as shown, or slats arranged in the vertical direction or a single horizontal slit running axially the length of the chamber. The open left and right horizontal sides 107 of the microfluidic channel allows forces to be applied to the TNCB specimen as illustrated by horizontal arrows 108 and 109 for the purposes of specimen positioning within the channel. In addition, any applied stress will also deform the tissue. For example, applying axial compressive stress (positive axial force) to the specimen will compress the tissue axially while expanding the tissue laterally, which can be used for sealing the edges of the tissue against the screen to prevent leakage. Applying a vacuum (negative axial force) to the specimen will elongate the specimen axially and slightly reduce diameter of the specimen laterally, which will allow reduction of the friction between the specimen and screen for axial movement. Only an axial segment of the TNCB and chamber are shown in FIG. 2A while the diameter of the TNCB specimen fills most of the cross-sectional area of the microfluidic channel. This setup can be used for all those types of specimen mentioned above; the only difference is that different fluid should be used for different type of specimen. For example, for TNCB the fluid are usually fixative, staining solution, while for live specimen, these fluid should be culture solution.

The sample chamber is designed to hold a delicate TNCB specimen that is long and slender for chemical preparation of the tissue for optical imaging. To allow monitoring of this process, lower surface 110 and upper surface 111 of the specimen chamber are made from optically transparent materials, such as glass or clear plastic (e.g. poly-methyl methacrylate, PMMA). Light source 112 can be used to transmit optical rays through the specimen as shown by arrows 113 and 114 which can be observed by eye 115 or measured using a photosensing device. Thus, the process of modifying the cells and tissue optical properties can be monitored optically during a series of separated steps involving chemical washes defined as fluid washes for chemical exchanges. In one step, the chemical staining process that stains the cell structures different colors (e.g. hematoxylin stains the nucleus blue) is monitored both by absorption and spectral measurements. In addition, the process of optically clearing the tissue for decreased light scattering is monitored by continuously measuring the light transmittance through the specimen chamber.

Figure 2B:
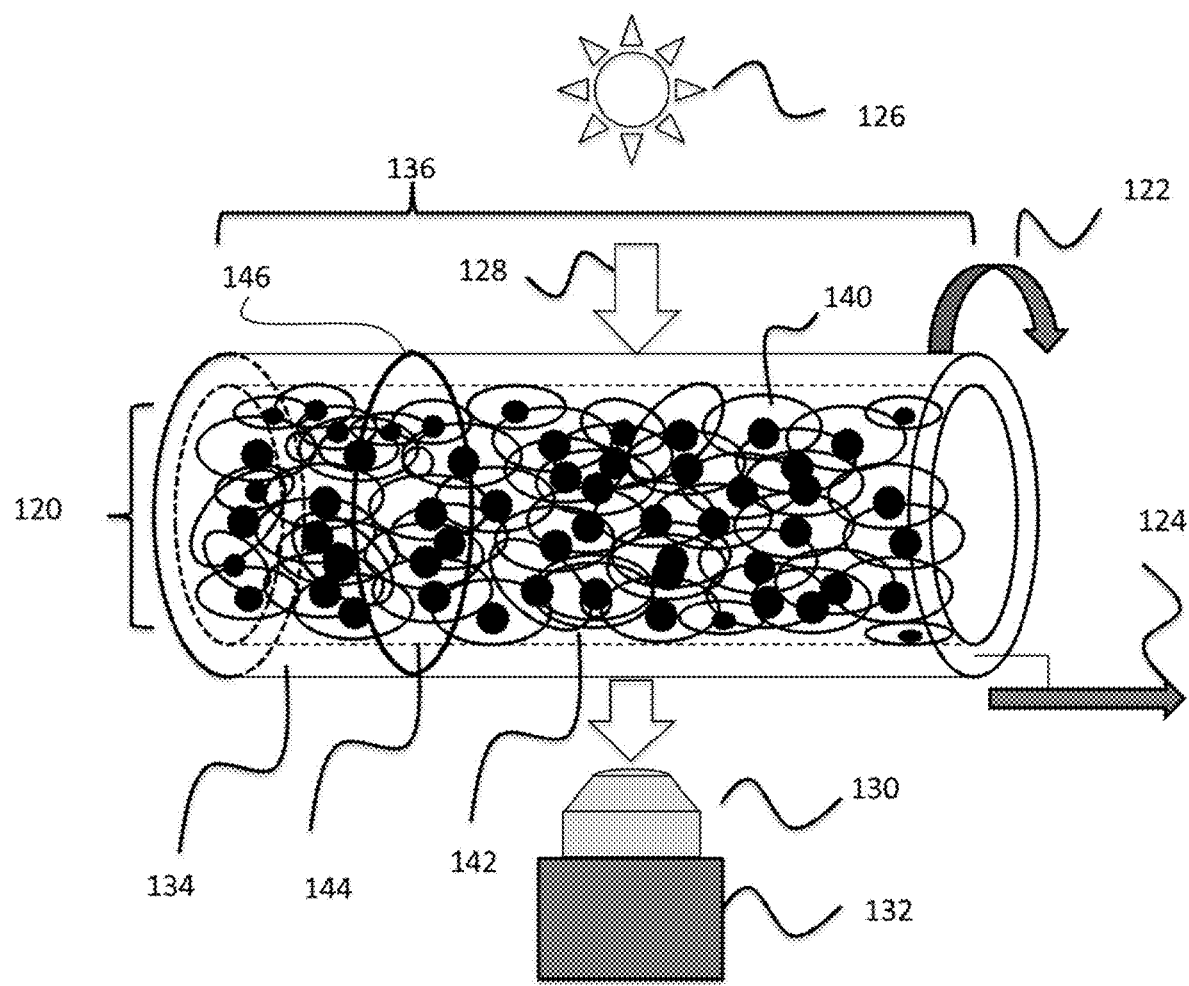
FIG. 2B schematically shows a segment of a tissue specimen filling the inner diameter of a transparent tube that will be rotated and translated under optical monitoring of these motions for the formation of a three-dimensional optical image of the specimen.

Referring now to FIG. 2B, there shown schematically is an example of a segment of TNCB specimen 120 being held within cylindrical transparent tubing 134 that will be rotated 122 and translated 124 for the formation of an optical image of the entire TNCB specimen. The refractive index of tube 134 should be as close to the refractive index of the specimen 120 as possible. Tube 134 should be substantially transparent to the signal from specimen 120. Although in FIG. 2B only transmitted light signal is shown, reflected light or fluorescence light can also be the signal. The wavelength of the signal can be from UV light to infrared depending on the property of the specimen and staining. The material of tube 134 can be glass (such as fused silica), plastic (such as acrylic, PMMA) and other material that's transparent in the wavelength range of signal from specimen. In order to image sub-cellular structure for diagnostic purposes, higher numerical aperture (NA>0.3) objective lens is used to image the tissue using white-light 126 in transmission 128 (arrows). These preferred objective lenses 130 also have higher magnification (>5×), so a camera can capture only a relatively small part of the tissue. For example, if we use a 40× objective lens and camera 132 with 1600×1200 pixels, the length of tissue within the recorded camera image is less than 0.5 mm. Because the minimum length of the TNCB tissue specimen is often desired to be 10 and 20 mm in length for improved diagnostic yield, the tube needs to be translated 124 so that different parts of the specimen can be imaged in time series to allow a complete image to be formed that is representative of the entire biopsy specimen. Tube 134 would have a length longer than the specimen so over 50 mm, and the material is optically clear with a smooth surface. Chosen materials are either a glass or plastic with refractive index chosen to help reduce refraction of the curved surfaces when immersed in fluid or gel. Similar to FIG. 2A, the diameter of the TNCB specimen fills most of the cross-sectional area of the channel, but only segment 136 of the entire axial length of the TNCB specimen and tube are shown in FIG. 2B. At the point of optical imaging, the specimen has been fully prepared. The tissue is composed of chemically fixed and stained cells 140 each having a nucleus labeled for high contrast optical imaging. The refractive index variations among cells and among the subcellular components have been reduced by the addition of optical clearing agents to the tissue. If imaging contrast agents are used for imaging, aqueous optical clearing solution that can preserve molecular specificity of binding to biological structures and preserve fluorescence optical marker performance should be chosen. Gaps 142 between tissue segment and tube inner wall 144 has been filled with optical clearing agents or embedding medium (not shown) that minimizes any refractive index differences between the tissue and tube material. The embedding media can be used to bind the tissue to transparent tube inner surface, making the tissue rigidly connected to the inside of the tube. To observe the tissue segment from all sides, the specimen and tube are rotated 122 with respect to a stationary observer or camera 132. During rotation, the relative lateral micromovements of the tube can be measured orthogonally to the tube axis by imaging the position of inner wall boundaries 144 over time by stationary observer 132. To observe the entire axial length of the TNCB specimen, the specimen and tube are axially translated 124 with respect to stationary observer 132 such as a digital video inspection computer system. During translation, the relative axial movement of the tube can be measured orthogonally to the tube axis by imaging the position of registration marker 146 located on the tube. This marker is shown as a painted line circumnavigating the tube outer diameter, which is located on the outside surface of the tube, but other types of registration markers and their locations are discussed in description of the optical imaging apparatus. The key point is that stationary observer 132 can optically monitor and record the concurrent axial translation and the rotation of the tube and specimen in order to correct for errors from a predetermined three dimensional trajectory, such a helical or twisted path.

Figure 2C:
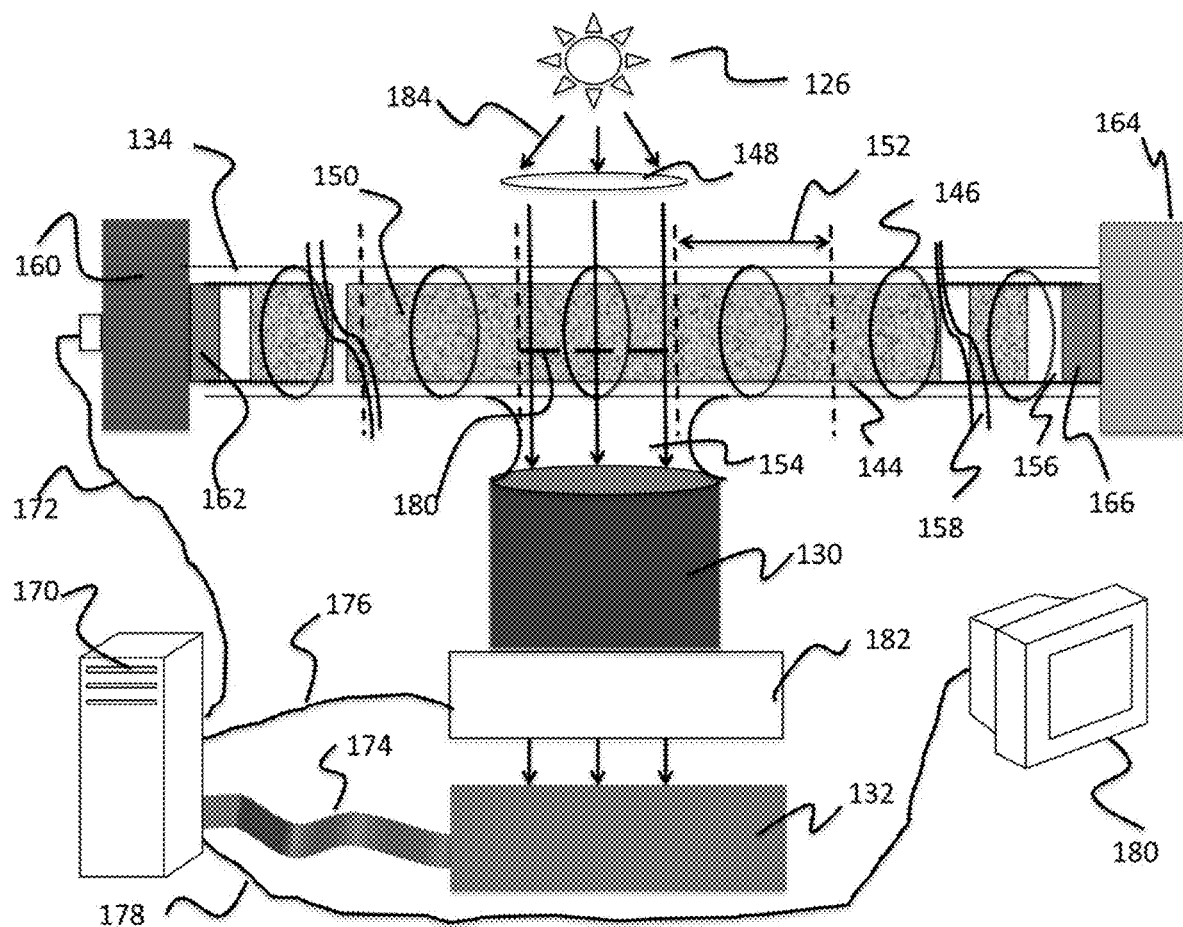
FIG. 2C schematically shows the full extent of the tissue specimen within a scaled tube for generation of a three-dimensional image of the entire specimen using a microscope system of focal scanning optical projection tomography.

Referring to FIG. 2C, there shown schematically is an example of TNCB specimen 150 being held within cylindrical transparent tubing 134 that will be rotated and translated as a single unit for the formation of a 3D optical image using the technique of focal scanning optical projection tomography. Tube 134 holding the tissue specimen has registration marks or axial scaling 146 along the length of the tube, either on the outside as shown in FIG. 2B or along the inner tube surface or within the tube wall. At least one registration marker is required for each axial segment 152 of tissue being imaged in order to maintain highly accurate imaging across the entire axial extent of the specimen. Although machine vision algorithms can track individual cells within a visual field, the ability to track a single cell within tissue cannot be reliably done for thick tissues and wide range of tissue types. Furthermore, the perspective of the 2D camera image will constantly change during the formation of a series of 2D images required for generating a single 3D image of the entire specimen using focal scanning optical projection tomography. Alternatively, fiducial markers can be placed within the tissue specimen during the preparation process, but maintaining consistent spacing across the entire axial length of the tissue is questionable. Clinical diagnosis will be compromised by the addition of an exogenous physical marker within the tissue.

Referring to FIG. 2C, a general embodiment of the 3D optical imaging system of the entire specimen 150 is exemplified by the subsystem components of motorized positioning 160 of the tube 134 which is connected and controlled by a computer system 172 and 170, respectively. The unshown part of specimen is indicated by axis break 158. There are gaps on each sides of specimen 150 to ensure that 162 and 166 doesn't affect imaging. Rotating and translation of the elongated tube is stabilized by solid clamping 162 between the tube and motor system 160 and mechanical joint 164 and 166. As discussed previously, monitoring of the tube motions are measured by optical imaging of the axial registration marks 146 and the edge between the inner tube wall 144 and specimen 150. Optical imaging is performed using a modified optical microscope in transmission mode, with white-light source 126 focused onto the specimen using a condenser lens system 148. The tube and lens systems are surrounded by optically transparent index matching medium (gel) 154 shown between the objective lens 130 and tube 134. The 2D image is acquired using an objective lens 130 and camera system 132 that is connected to a computer 170 using a high bandwidth electrical connection 174. Camera 132 is digital electronic camera, which can be either monochrome or color camera. The imaging focal plane 180 of the optical imaging system is shown within the specimen segment. The axial position of this focal plane 180 is determined by the focal scanning system 182 which is connected and controlled by a computer system 176 and 170, respectively. The focal scanning system moves the focal plane 180 along the optical axis of the microscope system by either scanning the position of the objective lens or by scanning the light beams 184 by a translating mirror (not shown).

To create 3D images, computer system 170 is used or any equivalent electronic device having appropriate processor and memory to accurately process, store and selectively access the plurality of digital images. Computer system 170 contains software, coding instructions and user instructions to process the generated projection images and 3D composite images. Computer 170 is coupled to provide control signals to motor system 160, focal scanning system 182 and camera 132. Tube rotation, focal scanning and camera should be synchronized. For example, the computer will send voltage signal through 172 to motor system 160 to rotate the tube at constant angular velocity, at the same time computer 170 will send continuous triangular wave voltage through 176 to PZT in scanning system 182 to scan the focal plane through the specimen periodically. During each scanning of PZT, computer 170 will turn on camera at the beginning of scanning to acquire image and turn it off at the end of scanning before transferring and storing the images in its memory cards. Computer system 170 acquires the 2D camera images with the recording of the location of the scanned focal plane within the tissue as the specimen is rotated and translated. There are two different methods of scanning, which will be described in detail in FIG. 6. One method is to continuously scan through the samples. In this case, the 2D images captured by the camera are projections, which can be used for 3D reconstruction. The other method is to scan through the specimen step by step to acquire a stack of 2D images. These 2D images are summed in computer to obtain one projection image. After acquiring projection images from different perspectives by either method, these projection images will be processed to reconstruct 3D images of the tissue segments. After reconstruction of each segment, all these 3D segments will be stitched together to generate a composite three-dimensional image of the entire specimen. Alternatively, a twisted trajectory of the scanned focal plane is followed by computer control and a complete 3D image is reconstructed from the series of processed camera images to form a single composite image of the specimen. Computer display 180 connected 178 to the computer system 170 is used to provide the user the ability to view this imaging process and visualize images that represent the specimen for diagnostic purposes. Because of the wave-like nature of light and limited acceptance angle of lens, the resolution is always poorer along the optical axis than laterally. The focal scanning methods described here can use lateral resolution from one view to compensate for the poor axial resolution from another view. This method can be applied to all imaging systems that have anisotropic resolution along two different directions independent of imaging modes, such as absorption, fluorescence, polarization et al.

Figure 3A:
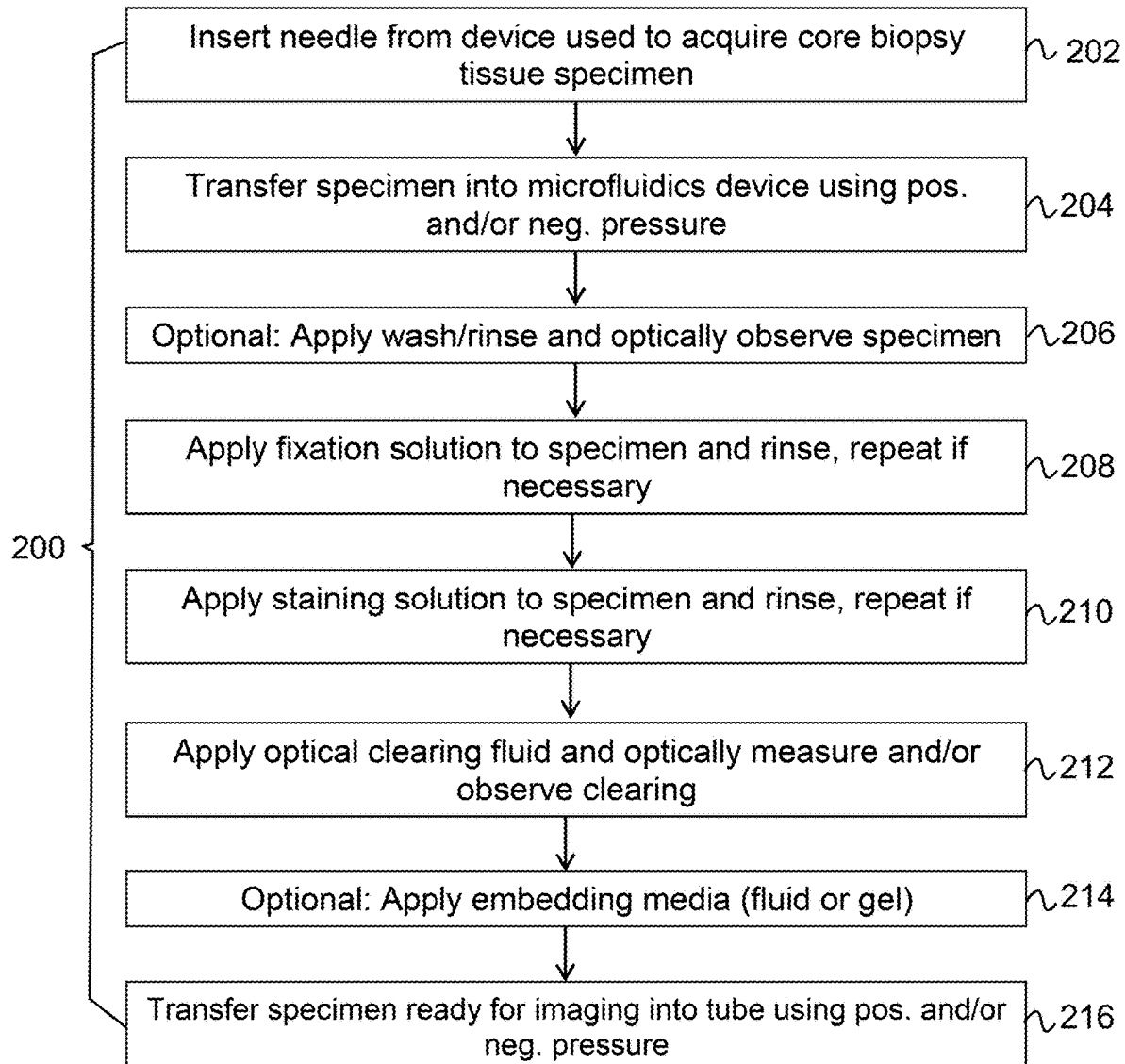
FIG. 3A schematically shows the example of a flow diagram for the process of TNCB specimen preparation for optical imaging using a series of fluid washes for chemical exchanges in a single specimen chamber of a microfluidics device.

Referring now to FIG. 3A, a first example of a flow diagram illustrating the specimen preparation process for 3D optical imaging while always maintaining the specimen is enclosed within a sample chamber as contemplated by an embodiment of the present invention is shown. As contemplated by one example of the present invention, a TNCB specimen is prepared for OPTM imaging using a microfluidics device, which allows for a series of fluid washes for chemical exchanges in a single specimen chamber. This first example of a specific sample preparation process 200 includes the steps of inserting the needle from a device used to acquire the TNCB specimen at step 202, transferring the specimen from the needle biopsy device into the microfluidics chamber at step 204, which can include positive pressure by pushing the specimen out of the needle using a plunger device, and/or pulling the specimen within the chamber from the needle by applying vacuum to the microfluidics chamber. All the plunger devices are cylindrical shape and 20-40 mm long. The following steps of 206, 208, 210, 212, and 214 are a series of fluid washes for chemical exchanges that pass through the TNCB specimen being held in the microfluidics chamber as schematically introduced in FIG. 2A. Step 206, is the optional step in the process of washing and/or rinsing the specimen in preparation of chemically fixing the tissue. In the case of a bloody specimen, the washing would remove the blood cells and hemoglobin dye molecules that attenuate light transmission. The optional washing step may preserve chemical specificity for a subsequent step of staining or labeling the tissue. Next step 208 is the application of a clear fixative solution for the disinfection and preservation of the internal structure of the biological tissue. Different chemical fixatives can be used for different purposes, such as formaldehyde-based mixtures (e.g. formalin), which preserve tissue structure and results in negligible tissue shrinkage. Alternatively alcohol-based mixtures (e.g. 50% ethyl alcohol in water) can be used to better preserve the chromatin structural detail inside the nucleus of the cell, but results in some overall tissue shrinkage. The application of fixative can be repeated in a series of applications, especially when increasing or decreasing the percentage of the fixative, e.g. formalin or alcohol.

In FIG. 3A, the next step 210 is the application of staining solution and subsequent rinses. The most common stain used for clinical diagnosis of disease is hematoxylin, which preferentially binds and darkens the nucleus over the cytoplasm when biological tissue is imaged under white light illumination. Eosin is the most common stain for the cytoplasm with a pink color contrasting with the blue hematoxylin-stained nucleus. There are various brands of hematoxylins and eosins and their formulae, which stain differently depending on the type and thickness of tissue, see Hine, I. F. (1981) "Block staining of mammalian tissues with hematoxylin and eosin," Stain Technology 56(2): 119-124. Since the microfluidics chamber has the ability to transmit light and monitor optical and spectral transmission, the staining can be continued in a single step or in a series of steps with subsequent washes until the optical characteristics have been achieved. Next step 212 is the application of optical clearing agent, which can be monitored by measuring the light transmittance change during time of immersion. The choice of optical clearing fluid applied to the specimen has several dependencies as discussed previously. However, a subsequent step 214 of applying an optically clear embedding media can be added that increases the adherence of the specimen to the inner surface of the transparent imaging tube. For example a gel may be applied that fills the spaces between the specimen and the transparent tube with a higher viscosity that also matches the refractive index of the transparent tube. Alternatively, a polymer fluid can be added that fills this same space, which is later hardened by curing (heat or ultra violet light) once the specimen is transferred into the transparent tube for imaging. The final step 216 is the transfer of the specimen prepared for optical imaging into a transparent tube that has been loaded into the microfluidics device. Again, there is the ability to use either positive pressure or negative pressure or the combination within the single channel as described for step 204.

Figure 3B:
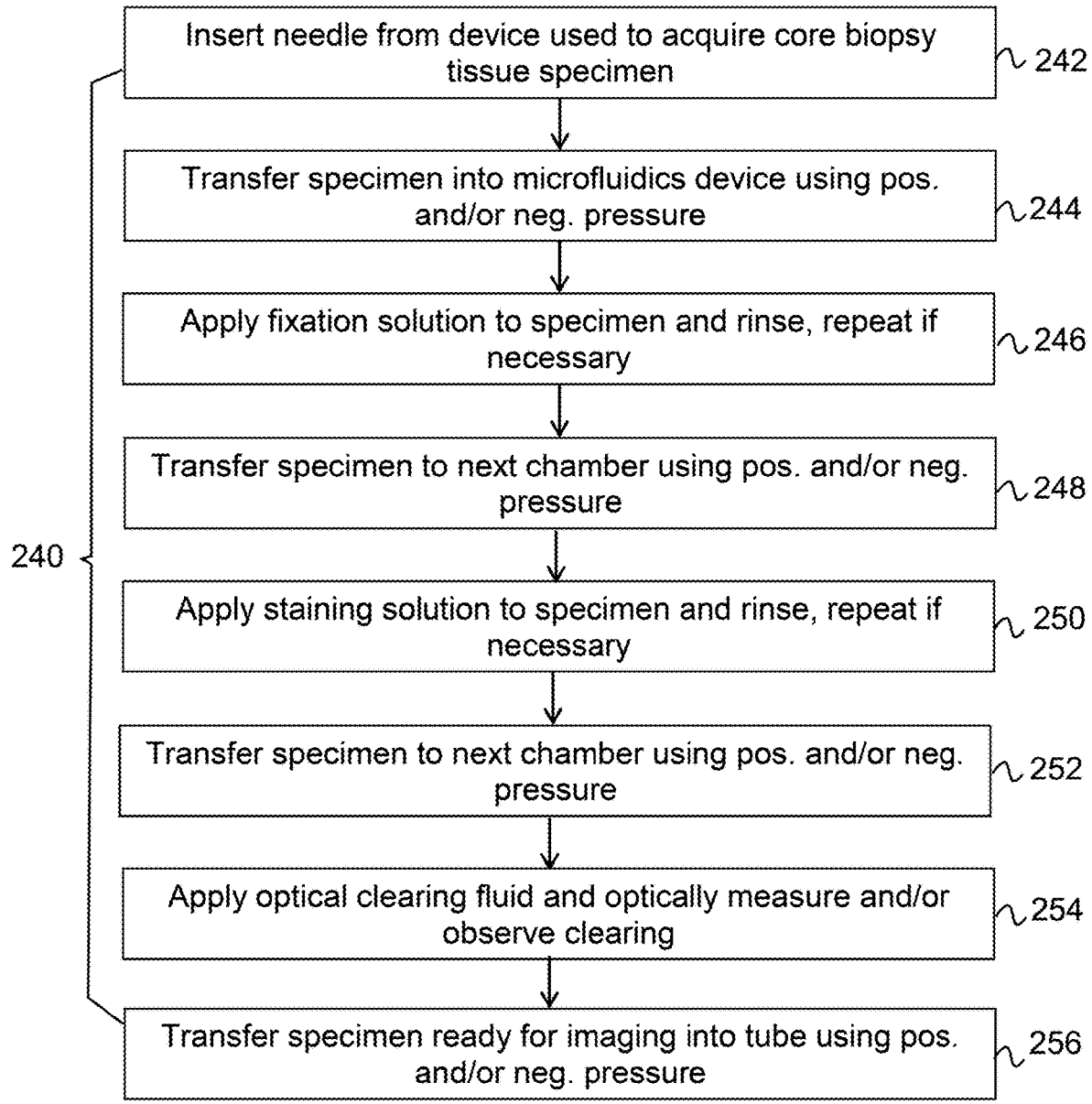
FIG. 3B schematically shows the example of a flow diagram for the process of TNCB specimen preparation for optical imaging using a microfluidics device with fluid washes for chemical exchanges in a series of specimen chambers.

Referring now to FIG. 3B, a second example of a flow diagram illustrating the specimen preparation process for 3D optical imaging while always maintaining the specimen is enclosed within a sample chamber as contemplated by an embodiment of the present invention is shown. As contemplated by one example of the present invention, a TNCB specimen is prepared for OPTM imaging using a microfluidics device, which allows for fluid washes for chemical exchanges in a series of specimen chambers. This second example of a specific sample preparation process 240 includes the steps of inserting a needle from a biopsy device used to acquire the TNCB specimen at step 242, transferring the specimen from the needle into the first chamber of the microfluidics device using positive and/or negative pressures within the channel at step 244, applying fixation solution to the specimen and optionally rinse at step 246, transferring the specimen to the next chamber in the series along the microfluidics channel at step 248, applying staining solution and rinsing, repeating if necessary at step 250, transferring the specimen to the next chamber in the series along the microfluidics channel at step 252, applying optical clearing fluid and optionally measuring or observing the clearing progress at step 254, and transferring the specimen prepared for optical imaging into a tube with positive and/or negative pressures at step 256.

Figure 4A:
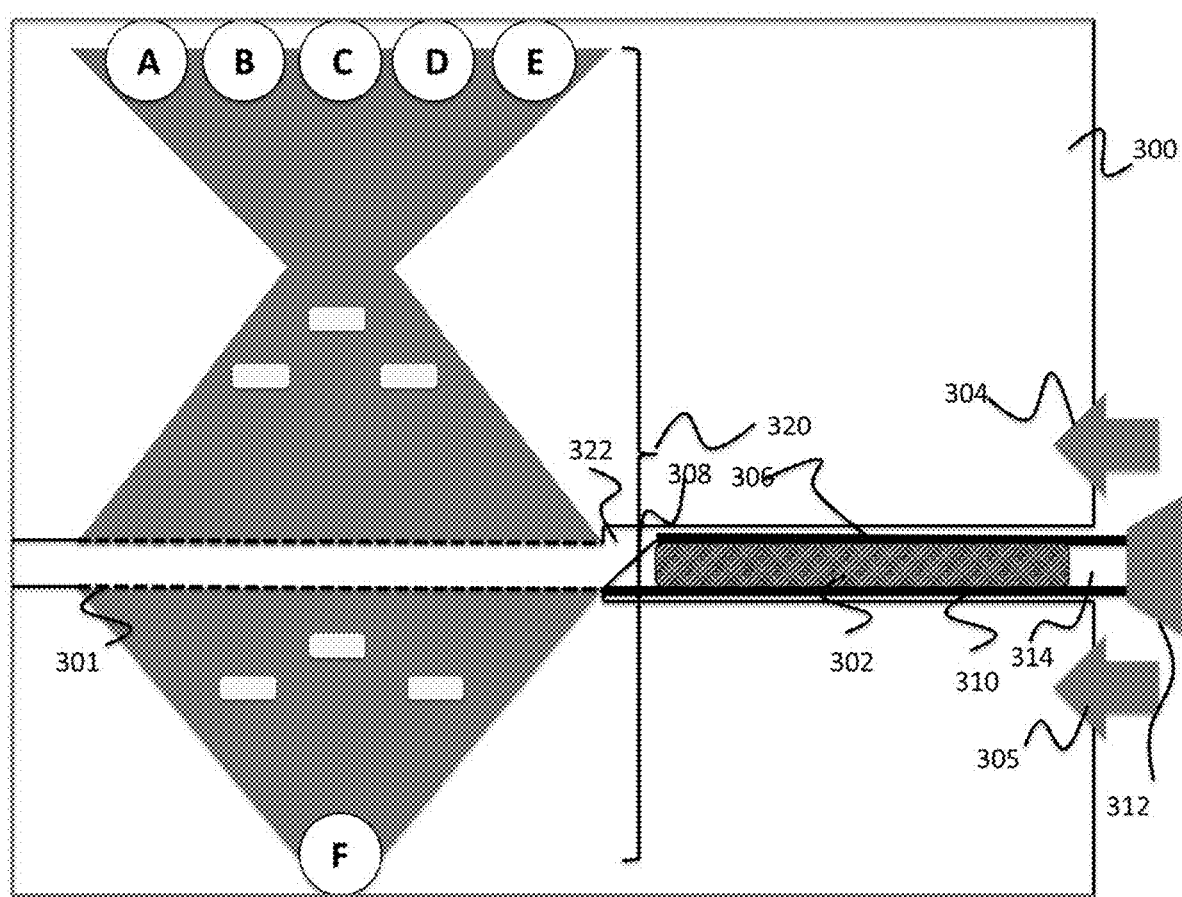
FIG. 4A schematically shows a microfluidics device having a single-specimen chamber that accepts the needle biopsy device for insertion (top-view).
Figure 4B:
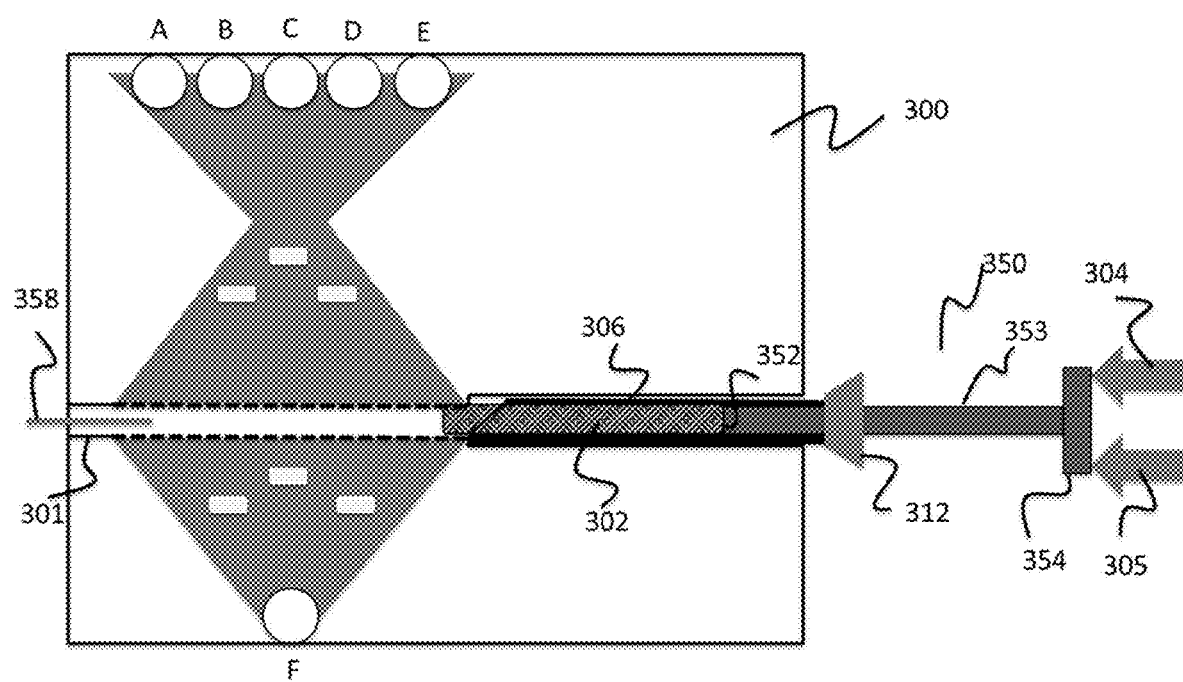
FIG. 4B schematically shows a TNCB specimen being transferred into the single-chamber microfluidics device for the preparation of tissue for optical imaging and diagnosis (top-view).

Referring now to FIG. 4A and FIG. 4B an example of microfluidics device 300 with a TNCB specimen being inserted into single specimen channel 301 used for preparing the tissue specimen for optical imaging, as contemplated by the present invention is schematically shown. In FIG. 4A, needle 306 from a biopsy device used to acquire TNCB specimen 302 is illustrated being inserted into microfluidics device 300 as illustrated by arrows 304 and 305. This fresh tissue specimen is fully enclosed in the lumen of needle 314. Needle tip 308 is inserted into enlarged channel access point for microfluidics channel 322 to be in close proximity with single specimen chamber 320 while needle base 312 is outside microfluidics device 300. Shaft of needle 310 is in close proximity to the enlarged entrance lumen of microfluidics channel 322 so that needle hollow lumen 314 is equivalent in size to specimen chamber 320. Needle 306 can be coupled to channel 322 by thread or luer lock. In FIG. 4B, plunger 350 is introduced through base 312 of needle 306. Plunger 350 is cylindrical shape and 20-40 mm long. Plunger 350 should tight fit into the inner lumen of needle 306. The material of the plunger can be metal, plastic, glass or ceramic. The choice of material depends on the fluid type used in the chamber. Tip of plunger 352 is making contact to the edge of TNCB specimen 302. Positive pressure or compressive force is being applied axially to specimen 302 when plunger 350 is moved into needle lumen 314 by forces applied to plunger cap 354, which are conveyed through plunger shaft 353. When tissue specimen is compressed axially, the material will expand laterally which is called the Poisson effect. Since this could cause binding of the specimen within the channel, a vacuum depicted as arrow 358 is applied on the opposite end of channel 301 to provide a counteractive effect, allowing transfer of specimen into the specimen chamber. A plunger applies force directly to the tissue surface; however, pressurized fluid such as water or air can also be applied.

Figure 5A:
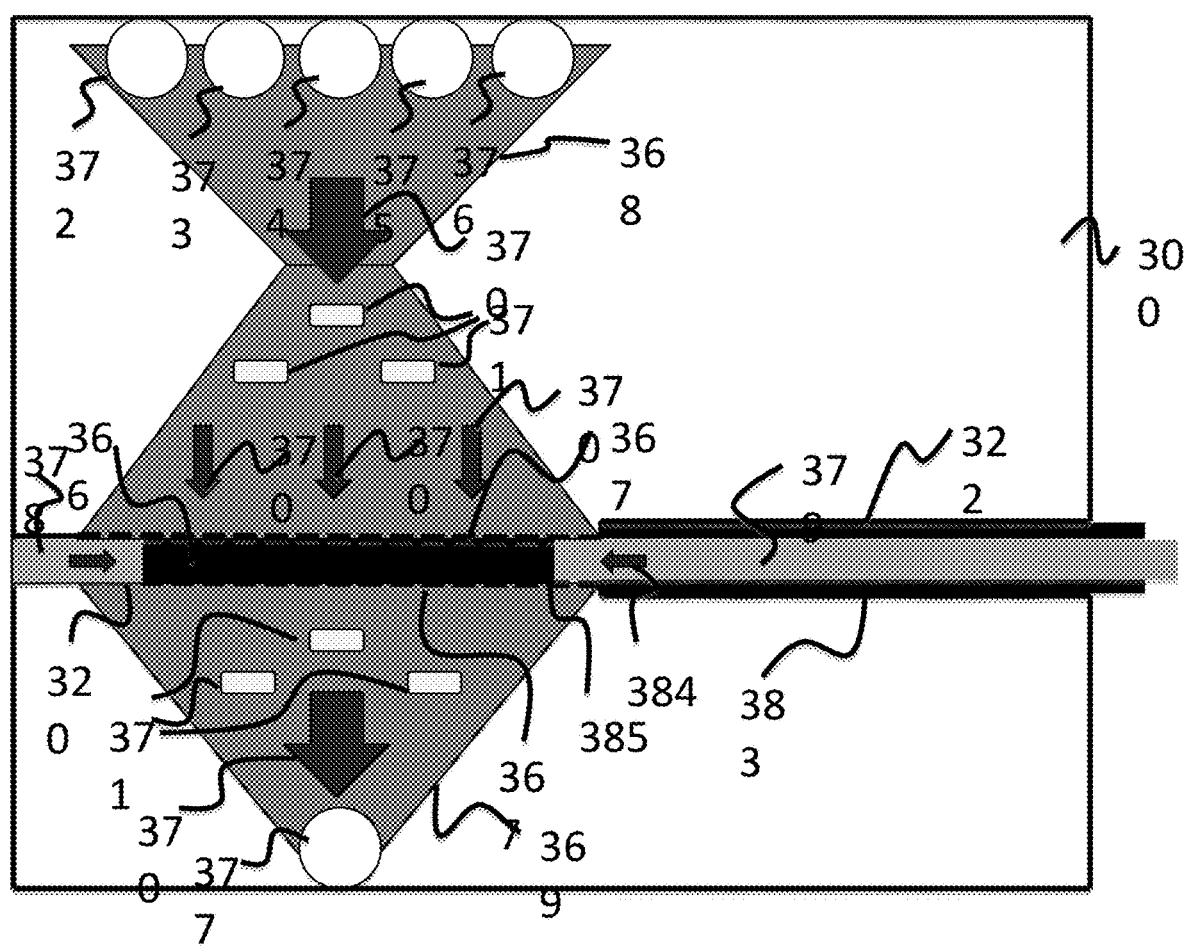
FIG. 5A schematically illustrates a series of fluids being applied to the TNCB specimen within the single specimen chamber in the microfluidics device with addition of compressive force applied to the two ends by axial motion of plungers in specimen chamber (top-view).
Figure 5B:
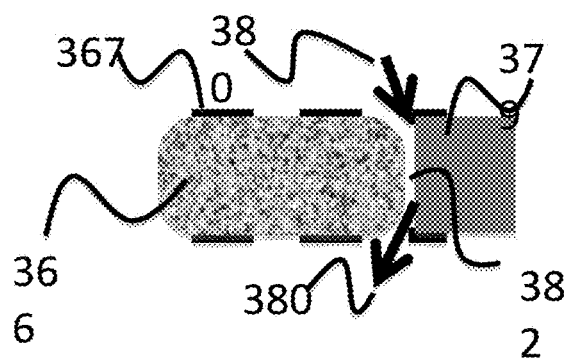
FIG. 5B schematically shows a magnified section of FIG. 5A illustrating the lack of sealing effects without adding compressive force to the ends of the specimen confined within the single specimen chamber device when fluids are applied (top view).
Figure 5C:
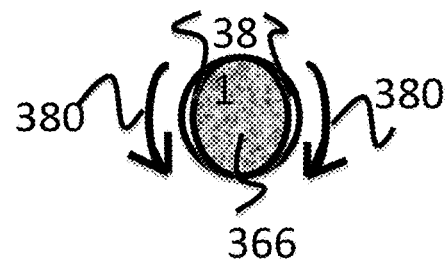
FIG. 5C schematically shows a magnified section of FIG. 5A illustrating the lack of sealing effects without adding compressive force to the ends of the specimen confined within the single specimen chamber device when fluids are applied (side view).
Figure 5D:
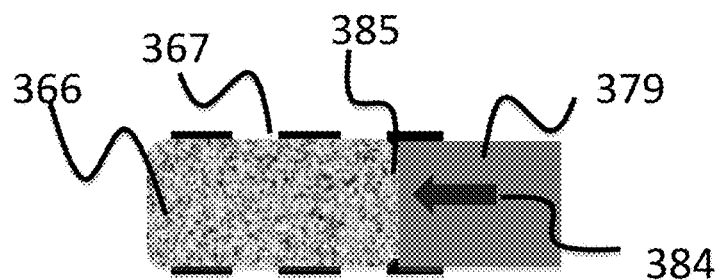
FIG. 5D schematically shows a magnified section of FIG. 5A illustrating the sealing effects with adding compressive force to the ends of the specimen confined within the single specimen chamber device when fluids are applied (top view).
Figure 5E:
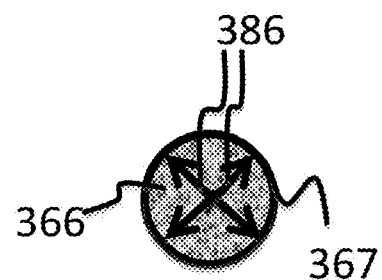
FIG. 5E schematically shows a magnified section of FIG. 5A illustrating the sealing effects with adding compressive force to the ends of the specimen confined within the single specimen chamber device when fluids are applied (side view).

Referring now to FIG. 5A and FIGS. 5B-5E an example of microfluidics device 300 with TNCB specimen 366 within single specimen chamber 320 having one of a series of fluid washes for chemical exchanges in preparation of optical imaging, as contemplated by the present invention is schematically shown. In FIG. 5A, tissue specimen 366 is located in single specimen chamber 320 which has screen 367 separating tissue 366 from microfluidics input 368 and output 369 structures that are much wider than the single specimen channel. Fluid flow in the direction of the input and output from the specimen chamber is shown by vertical arrows 370. Within the input and output fluid channels are obstacles 371 to fluid flow that are placed to enhance mixing and spreading of fluid across the wide channels. A series of fluid inputs to the microfluidic device are labeled 372, 373, 374, 375, and 376, which are connectors for external sources of fluid. A single connection for outflow or waste fluid from the microfluidic device is labeled as 377. When not in use these ports have a valve (e.g. ball or disk valve design as used on heart valve replacement) that allows only positive pressure flow and no back flow. Vacuum can be applied to lock these valves shut.

When TNCB specimen 366 is located within single specimen chamber 320 of FIG. 5A, but before fluid is input and exchanged on microfluidic device 300, two plungers 378, 379 are introduced axially 384 into single specimen channel 367 from opposite ends until they touch the tissue specimen 385. In FIGS. 5B-5E, two tissue conditions are contemplated when fluid is input and forced to immerse and flow through specimen 366: (1) no axial positive pressure is applied to compress the specimen shown in FIGS. 5B and 5C, and (2) positive compressive pressure 384 is applied using plunger 379 shown in FIGS. 5D and 5E. In case (1), fluid 380 can more easily squeeze between ends 382 of tissue 366 and plunger 379, and move around the circumference of specimen sides 381, as illustrated in the FIG. 5B top-view and FIG. 5C side-view schematics, respectively. In case (2), plunger 379 is compressing tissue 366 axially 384 causing the tissue to expand laterally 386, which makes the fluid unable to pass either around ends 382 or sides 381 of specimen 366, as illustrated in the FIG. 5D top-view and FIG. 5E side-view schematics, respectively. Accurate and precise application of positive pressure may be required, so feedback force and/or servo control of plungers 378 and 379 would be necessary to not damage tissue. Once specimen 366 is held tightly 385 within specimen chamber 320, then the series of fluid washes for chemical exchanges can be done with certainty that predictable outcomes will result from the most important steps in sample preparation, i.e. the fixation, staining, and clearing protocols.

As an illustrative example embodiment that follow the process shown in FIG. 3A, a series of fluid inputs to microfluidic device 300 are labeled 372, 373, 374, 375, and 376 in FIG. 5A which are tubing connectors for external sources of fixation, staining, clearing, rinsing, and embedding fluids, respectively. Fixation step 208 will be the application of ethyl alcohol solution in increasing percentage of alcohol that pumps this fixative solution through input port 372, and through the tissue specimen in the specimen chamber. Staining step 210 will be the application of hematoxylin solution through input port 373, followed by rinse solution through input port 375. Clearing step 212 will be the application of methyl salicylate solution through input port 374, and through the tissue specimen in the specimen chamber. Finally, input port 376 can be reserved as a back-up port, or any washing or embedding step 214. All fluid waste will be output from the microfluidics device through port 377, and a second port (not shown) can be used to increase flow-rate and provide a back-up port. Since not all fluids are miscible with each other, each step listed above can be broken up into a succession of graded solution mixtures of ethanol for adding or removing water to/from the specimen 366. Since the tissue will not be handled immediate disinfecting and strengthening the tissue specimen with fixative is no longer considered a necessary first step in the sample preparation process. Therefore now processes will be developed that stain the tissue first, followed by fixation, clearing, and possible embedding.

Referring again to FIG. 5A, the needle previously inserted into the microfluidics device was replaced with transparent tube 383 to be used for 3D optical imaging in the same enlarged channel 322. This is just one embodiment of a microfluidic device design that uses a single specimen chamber for fluid washes for chemical exchanges. A second embodiment (not shown) uses an enlarged channel on the opposing side of the single specimen channel, which holds the transparent tube for 3D optical imaging. The advantage of this second embodiment is that enlarged microfluidic channel 322 can be custom sized only for the one tubular structure holding and transporting TNCB specimen 366. For example, the thin needle is made from a thin-walled metal tube, which is expected to be slightly smaller in outer diameter than the transparent tube for 3D optical imaging. Enlarged channel 322 on one side of microfluidic device 300 that accepts this needle insertion can be slightly smaller in diameter than enlarged channel 322 on the opposing side of single specimen channel 301 that holds the transparent tube for 3D optical imaging. Whereas, in FIG. 5A, enlarged channel 322 and entrance port may sleeve around the needle to achieve a snug fit inside microfluidics device 300. Sleeve 384 may be one of several different wall thicknesses while having the same outer diameter to match that of transparent tube 383 to compensate for various wall thicknesses used in biopsy needles. Optionally, sleeve 384 has a secondary purpose of extending to encompass the sharp tip of the needle so that a blunter end is exposed to the microfluidic device channel and the personnel handling the needle. Note that sleeve 384 was not shown around the needle shaft in FIGS. 4A and 4B.

Figure 6:
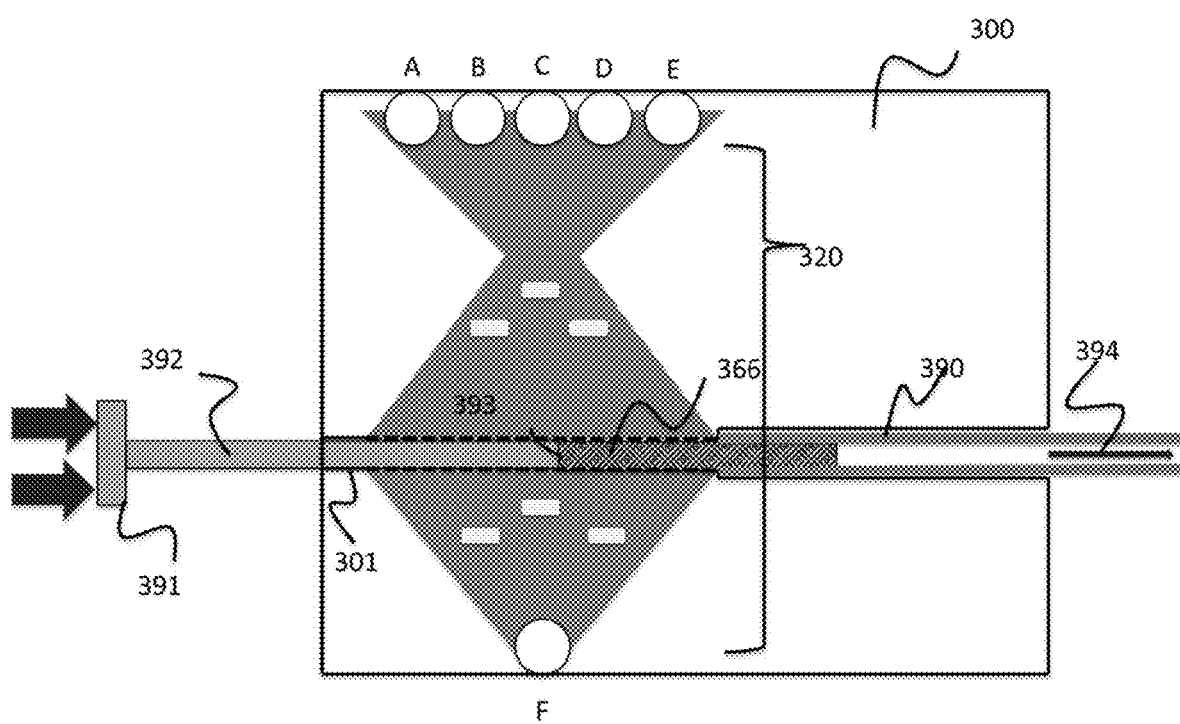
FIG. 6 schematically shows the tissue specimen being transferred out from the single chamber of the microfluidics device into the transparent tube for optical imaging (top view).

Referring now to FIG. 6 an example of microfluidics device 300 with TNCB specimen 366 being transferred out of single specimen chamber 320 and into transparent tube 390 used for 3D optical imaging, as contemplated by the present invention is schematically shown. In FIG. 6, tissue specimen 366 is shown part way out of single specimen chamber 320 and part way into transparent tube 390 designed to hold specimen 366 for 3D optical imaging. This FIG. 6 is the last in a series of Figures (FIGS. 4A, 4B, and 5A) describing the microfluidics system that uses a single specimen chamber, single specimen channel, and a single enlarged channel entrance to accommodate a needle and transparent tube 390 for specimen transfer. The axial movement of TNCB specimen 366 within the single channel is produced by forces applied to plunger cap or base 391. Positive pressure is exerted on the end of tissue 366 through plunger shaft 392 by direct contact with the end face of plunger tip 393. Alternative means for applying positive pressure on specimen 366 for movement within microfluidics channel 301 can be the application of fluid pressure (air or liquid), which can replace mechanical means, such as the plunger. To help counteract the tissue expansion laterally, which will restrict axial sliding of the specimen, vacuum 394 (depicted as an arrow) is applied to the opposite end of the channel. The application of negative pressure can be conveyed to the specimen mechanically, by withdrawing a second plunger (not shown) that is moving axially within the transparent tube. During specimen transfers, the ports A to F can be sealed, although positive fluid pressure could be used to compress the tissue and help release from the screen in the specimen chamber.

Figure 7A:
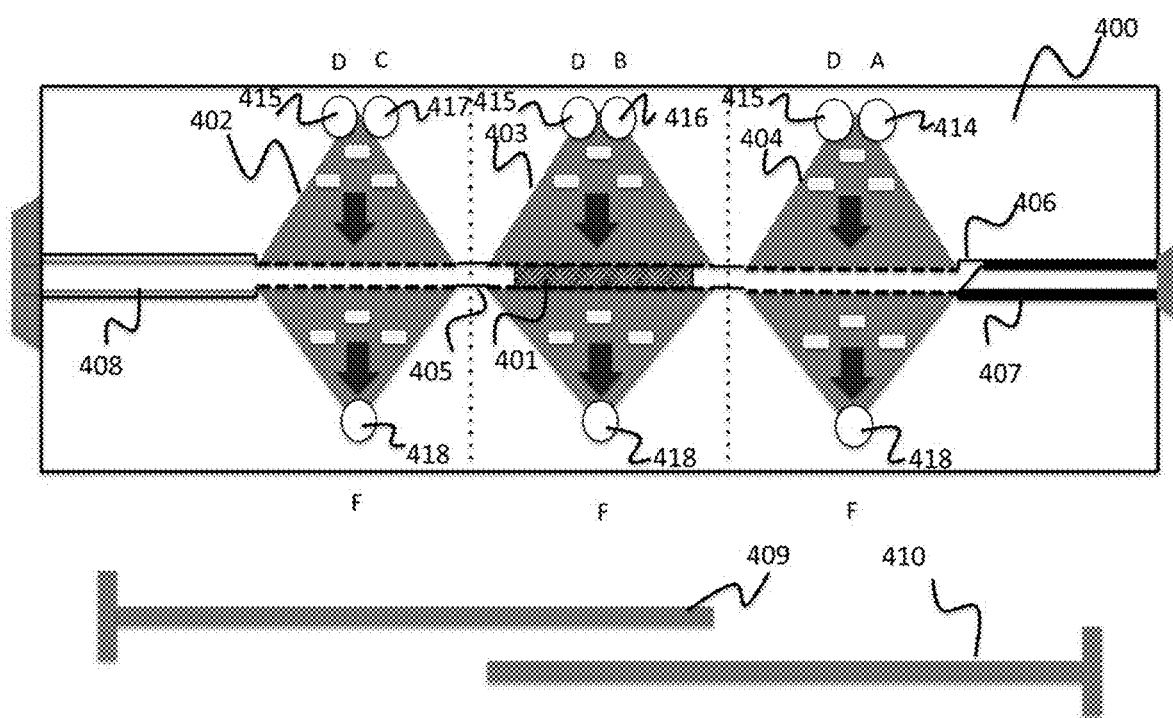
FIG. 7A schematically shows a microfluidics device having a line of specimen chambers from a biopsy needle on one side to a transparent tube on the other side. Each of the three chambers is used for separate processing steps in series. A TNCB specimen is shown in the center chamber with plungers shown for applying compressive pressure to the ends of the specimen (top view).
Figure 7B:
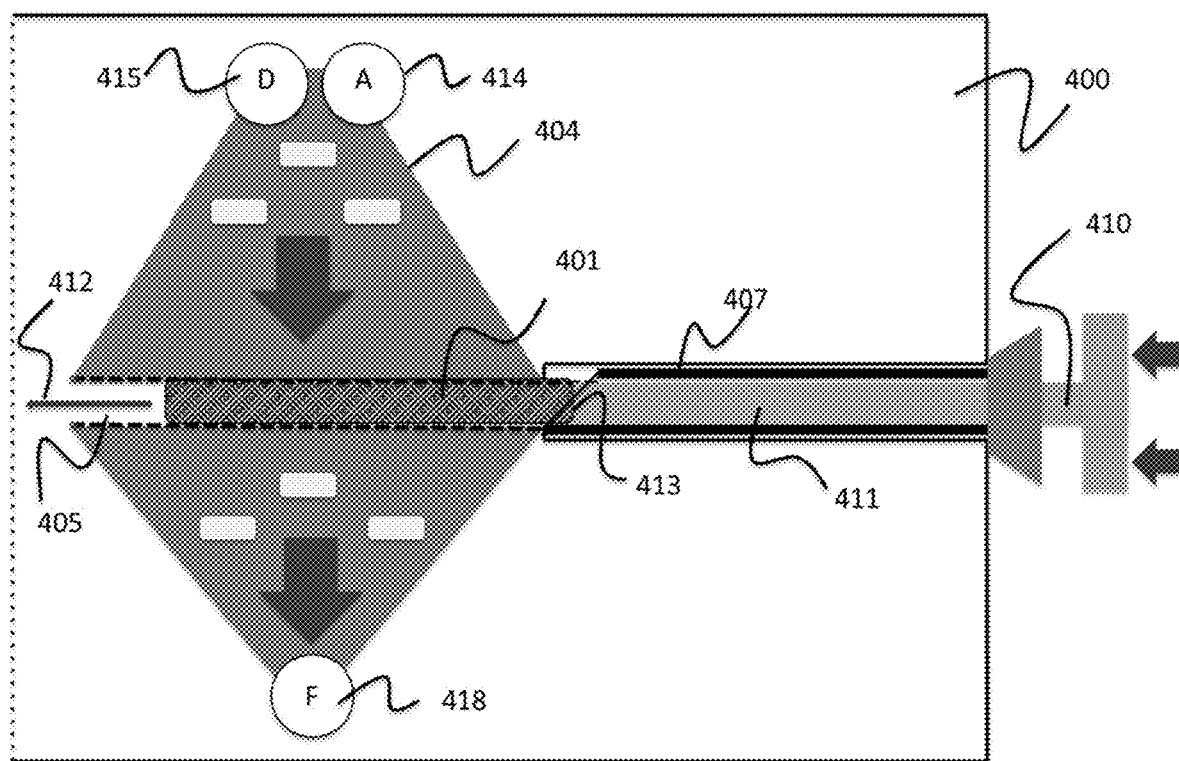
FIG. 7B schematically shows a TNCB specimen being inserted from the biopsy needle to the first specimen chamber using a plunger (top view).
Figure 7C:
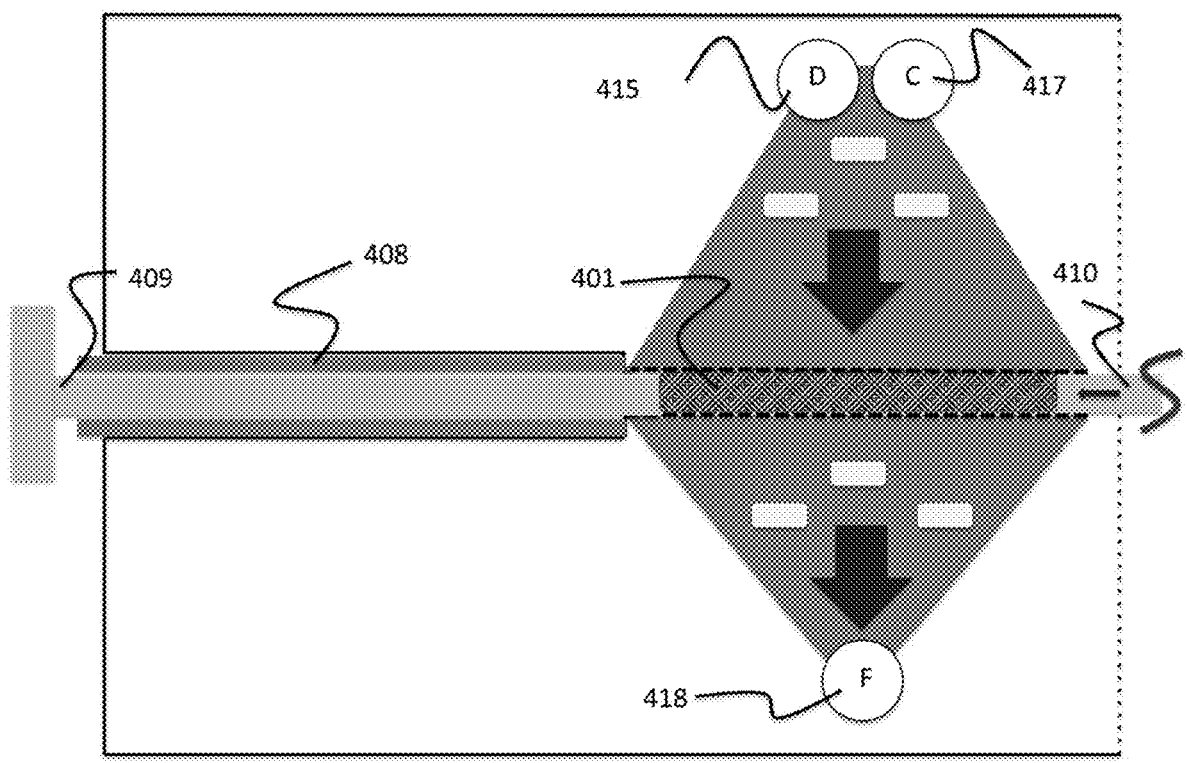
FIG. 7C schematically shows a TNCB specimen in the third of the series of three specimen chambers as compressive force is being applied at both ends while fluids are pushed through the specimen (top view).

Referring now to FIG. 7A, FIG. 7B, and FIG. 7C an example of microfluidic device 400 consisting of single channel 405 with a series of three specimen chambers used for a series of fluid washes for chemical exchanges in preparation of optical imaging, as contemplated by the present invention is schematically shown. In FIG. 7A, microfluidic device 400 is shown with TNCB specimen 401 contained in center chamber 403 of three specimen chambers within single specimen channel 405. In this example, enlarged entrance ports 406 of microfluidic device 400, which accepts biopsy, needle 407 and transparent tube 408 for 3D imaging are on opposing sides of single channel 405 of microfluidics device 400. This design has the advantage of allowing these enlarged channel entrances to have different features, such as different sizes (e.g. diameter and length) and surface coating (e.g. hardness, opacity, smoothness, hydrophobicity). When needle 407 and transparent tube 408 are inserted into microfluidics device 400, the inner diameter of single channel 405 can be of approximately the same cross-sectional area. In this case, single plungers can be used throughout the length of the microfluidic device or as a pair of plungers 409, 410. The ports for fluid input and output are limited to two and one, respectively for this example with an example procedure that follows the flow chart in FIG. 3B listed below.

In FIG. 7B TNCB specimen 401 is transferred from needle 407 from a biopsy device to within the first of three specimen chambers 404 using positive pressure from plunger 410 inserted into needle lumen 411 and negative pressure (vacuum) 412 is applied to the opposite side of single specimen channel 405, see arrow. Plungers are inserted into both sides of the specimen channel and advanced axially to make contact with the ends of the specimen (not shown). Appropriate positive pressures are applied to tissue ends 413 to seal the entire tissue specimen 401 within the first specimen chamber 404 for fluid washes for chemical exchange. Fluid port 414 is unsealed and a fixative solution is flowed into the wide fluid channel while fluid port 415 is opened to remove waste. Fluid port 415 is opened to allow washing, rinsing, or dilution functions to the fixation step. In FIG. 7A, specimen 401 has already been moved into the second 403 of three specimen chambers using positive and negative pressures from either plungers or fluid pressures, or their combination (not shown). After sealing tissue specimen 401 within second specimen chamber 403, fluid ports 416, 415, and 418 are opened to allow fluid washes for chemical exchanges and staining of tissue specimen 401. In FIG. 7C specimen 401 is transferred into third chamber 402 of three specimen chambers using plungers 409 and 410 and optionally fluid pressure within the wide fluid chamber. Once tissue specimen 401 is sealed within the third specimen chamber 402, fluid ports 417, 415, and 418 are opened to allow fluid washes for chemical exchanges and optical clearing of tissue specimen 401. One or more additional stages with specimen chambers are not shown but can be added to this multistage design of a microfluidics device. After specimen 401 is fully prepared for optical imaging, specimen 401 is transferred into transparent tube 408 for 3D optical imaging. It is contemplated that this multistage microfluidics device may be attached directly to the 3D optical imaging instrument, so the microfluidics device is removed to continue the process of creating a single image representative of the entire TNCB specimen.

Figure 8A:
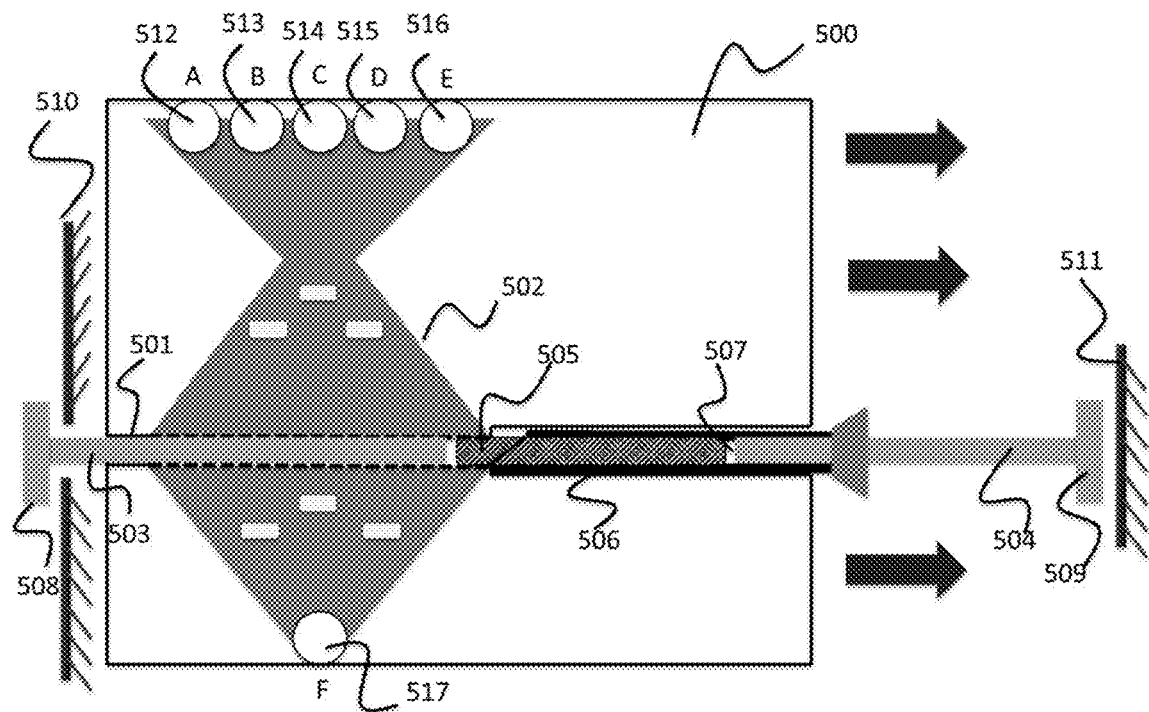
FIG. 8A schematically shows a TNCB specimen being transferred from a biopsy needle into a single-chamber by moving the microfluidics device using a two plunger system of pushing and pulling by creating a vacuum (top view).
Figure 8B:
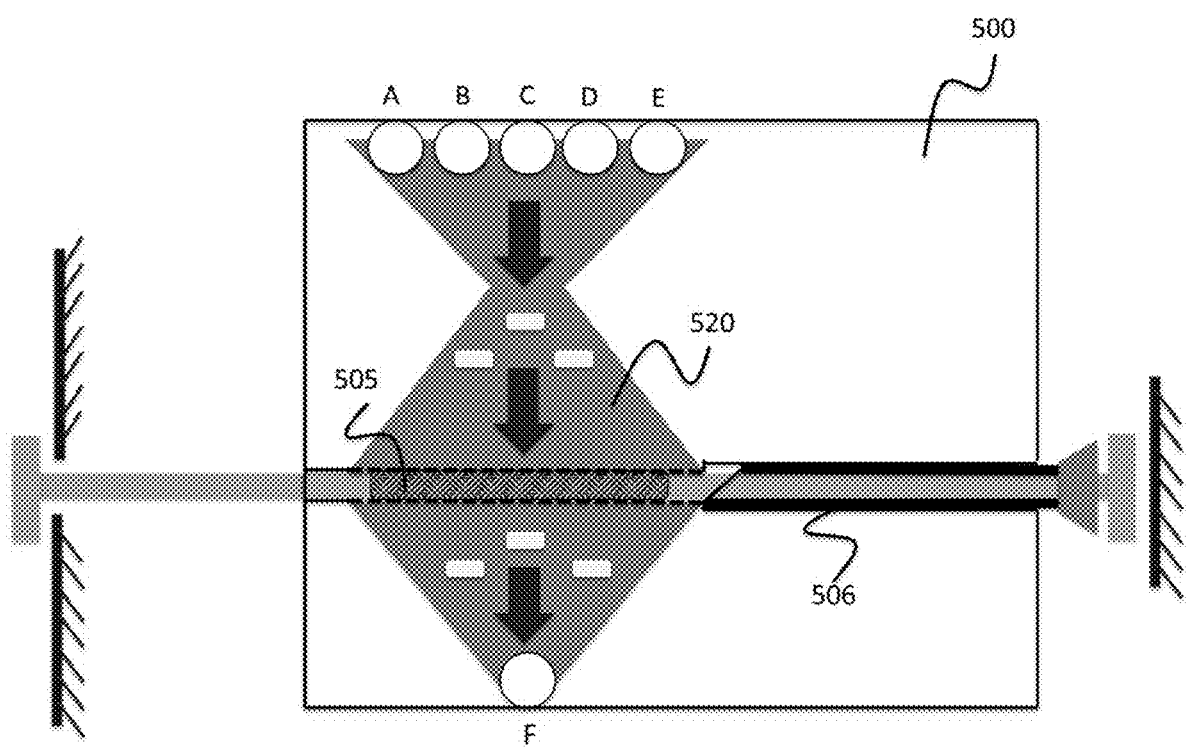
FIG. 8B schematically illustrates a series of fluid washes for chemical exchanges through the TNCB specimen is illustrated in the single-chamber microfluidics device of FIG. 8A (top view).

Referring now to FIG. 8A and FIG. 8B an example of microfluidics system 500 consisting of single channel 501 and specimen chamber 502 with dual plungers 503, 504 for manipulating TNCB specimen 505 in a semi-automated process of sample preparation for optical imaging, as contemplated by the present invention is schematically shown. In FIG. 8A, tissue specimen 505 is shown being inserted from needle 506 into a single specimen chamber microfluidics device using a two plunger system. Plunger 504 is moving axially within needle lumen 507, behind specimen 505, generating positive pressure on the specimen, whereas opposing plunger 503 moves ahead of the specimen generating negative pressure on the other end of the specimen. Both plungers 503, 504 do not need to make contact with the ends of tissue specimen 505 as these pressures can be conveyed by fluid coupling. Since both plungers 503 and 504 move in synchrony, the one microfluidics device may be moved rather than the two plungers. The two plungers 503, 504 are moved according to the positions of each of the two plunger bases (or caps) 508, 509 relative to fixed supports 510, 511. Plunger 504 leads the axial movement of specimen 505 and may be adjusted to move earlier than trailing plunger 503 to reduce friction and the Poisson effect on the tissue specimen 505. In FIG. 8B, wide fluid channels 520 may be pre-infused with fluid of appropriate chemistry (e.g. osmolarity) to facilitate rapid low-friction and tissue damage of the transfer of specimen 505, and to facilitate rapid fluid washes for chemical exchange with the tissue. For example the fluid could be flowing slowly during insertion with aqueous solution of lower osmotic pressure and with surfactant to help wash away blood and reduce bubbles. Needle 506 can also be flushed clean in the process of insertion. Not shown is the transfer of tissue specimen 505 back into the same needle 506 after the sample processing steps. This is an alternative procedure of transferring the TNCB specimen to the 3D optical instrument. Prepared TNCB specimen 505 can be loaded directly into the transparent tube already mounted on the 3D optical imaging instrument. This has the advantage of handling only the metal needle and not handling the specimen tube, which is a more delicate (glass) tube with optically smooth and clean surfaces.

Figure 9:
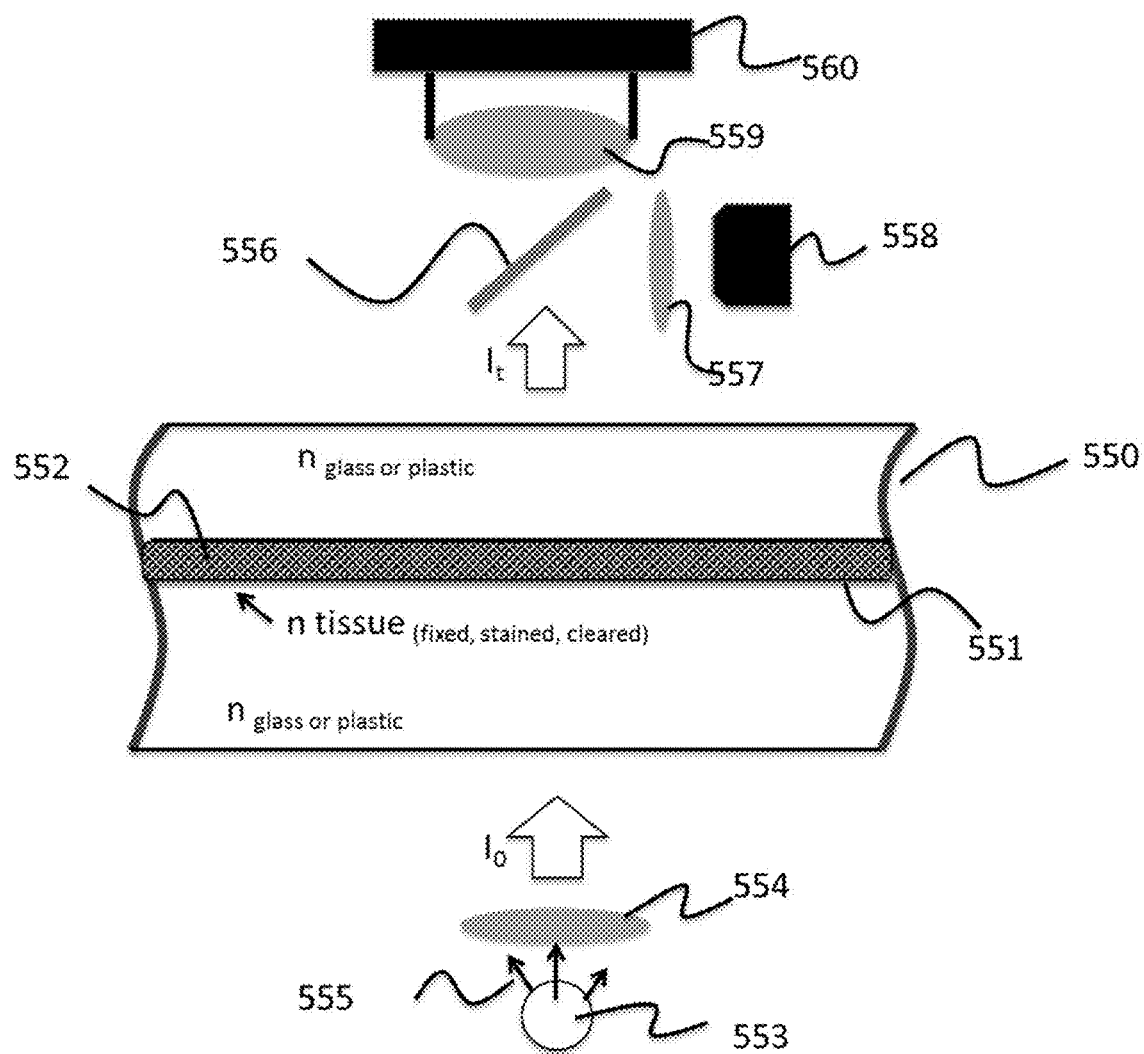
FIG. 9 schematically shows a TNCB specimen being observed optically using a transmission optical system to determine adequacy of the specimen and quality of sample preparation (side view).

Referring now to FIG. 9 an example of microfluidics device 550 apparatus consisting of single channel 551 as a specimen chamber used for observing and measuring the optical parameters (transmittance/absorbance, fluorescence/spectral properties) of TNCB specimen 552 in preparation of optical imaging, as contemplated by the present invention is schematically shown. Previously microfluidics devices 300, 500 with a single specimen chamber have been described with a needle and transparent tube interchanged on one side, on separate sides, or only the needle being inserted into the microfluidic device. In these designs, a single optical system can be arranged over the clear specimen chamber with an optical axis orthogonal to the axes of lateral fluid flow and axial specimen movement in the channel. In FIG. 9 an embodiment of a single optical measurement system is illustrated. Light source (such as a light emitting diode) 553 is located underneath microfluidics specimen chamber 550 and optical detection is located above specimen chamber 550. In one embodiment, the change in transmittance ($I_o$ to $I_t$) from optical clearing is measured with lens 554 collimating light 555 from source 553 through specimen 552 within specimen chamber 550. Optical beamsplitter 556 (partly reflective glass or filter) directs at right angle, a known fraction of this light to lens 557 and detector 558 (photodiode) for real-time measurement of transmittance. Alternatively camera 560 shown above the beamsplitter can measure the image luminance and spectral properties of the image of tissue specimen 552. This information can help automate the sample preparation process and also increase the consistency of the sample preparation at one or every step in the process exemplified in FIGS. 3A and 3B.

Figure 10A:
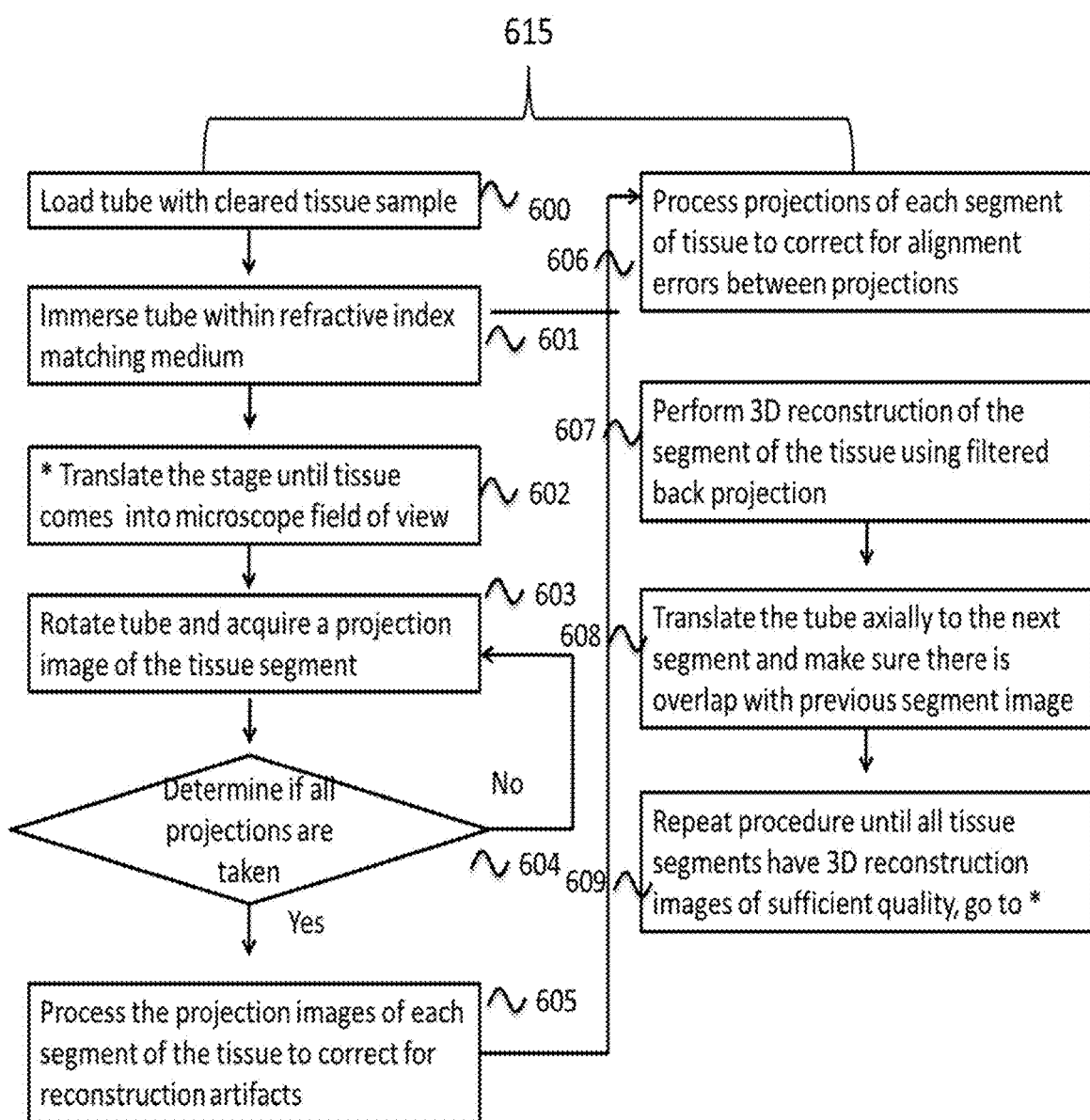
FIG. 10A schematically shows an example of a flow chart for the process of TNCB specimen imaging using optical imaging method of creating a series of 3D image reconstructions.

FIG. 10A shows a flow diagram for the process 615 of TNCB specimen imaging using OPTM method for series of 3D image reconstructions. The tissue specimen is prepared in microfluidic device and loaded into the tube for imaging at step 600. The tube is surrounded by refractive index matching medium to reduce aberration and image distortion at step 601. The region of interest in the tissue is translated into the field of view by translational stage at step 602. Then the focal plane is scanned through the specimen to produce projection images while the motor at step 603 rotates the tube. Projection images obtained from step 603 can be taken step by step or continuously. If projection images are to be taken step by step, the step motor rotates the tube to a new position and stops before the PZT scanner generates one projection. If projection images are to be taken continuously, PZT scans the specimen much faster than the rotation of the tube so that each projection image can be considered as from one specific perspective with little blur. Projection images can also be generated by different means. One way is to integrate all the light on the camera incoherently during one scanning period. The other way is to take a stack of images during one scanning and add all these images to produce one projection image using computer calculation. Whether enough projection images for one segment are taken is determined at step 604. To enhance image quality, 2D deconvolution can be performed to each projection image at step 605. The projection images in one set are aligned to correct mechanical errors at step 606. The projection point spread function (PSF) used in deconvolution can be either obtained by simulations or experimental measurements. If the projection image is generated by adding a stack of images, the deconvolution can also be performed on each slice before adding them to produce one projection image. One advantage of using stacks is that many artifacts, such as non-uniform illumination throughout the specimen can be corrected, while the disadvantage is that it is more time-consuming. The 3D image is reconstructed by using filtered back-projection at step 607. After all the projection images from one full rotation are taken, whether the whole tissue has been imaged needs to be determined at step 608. If the end of the tissue hasn't been reached, the next part of tissue is moved into the field of view for imaging at step 609. It needs to make sure that there is overlapping area between these two sets of images so that common features can be found to stitch them together. This will continue until all desired parts of the tissue have been imaged. The images of each part of the tissue are processed individually.

Figure 10B:
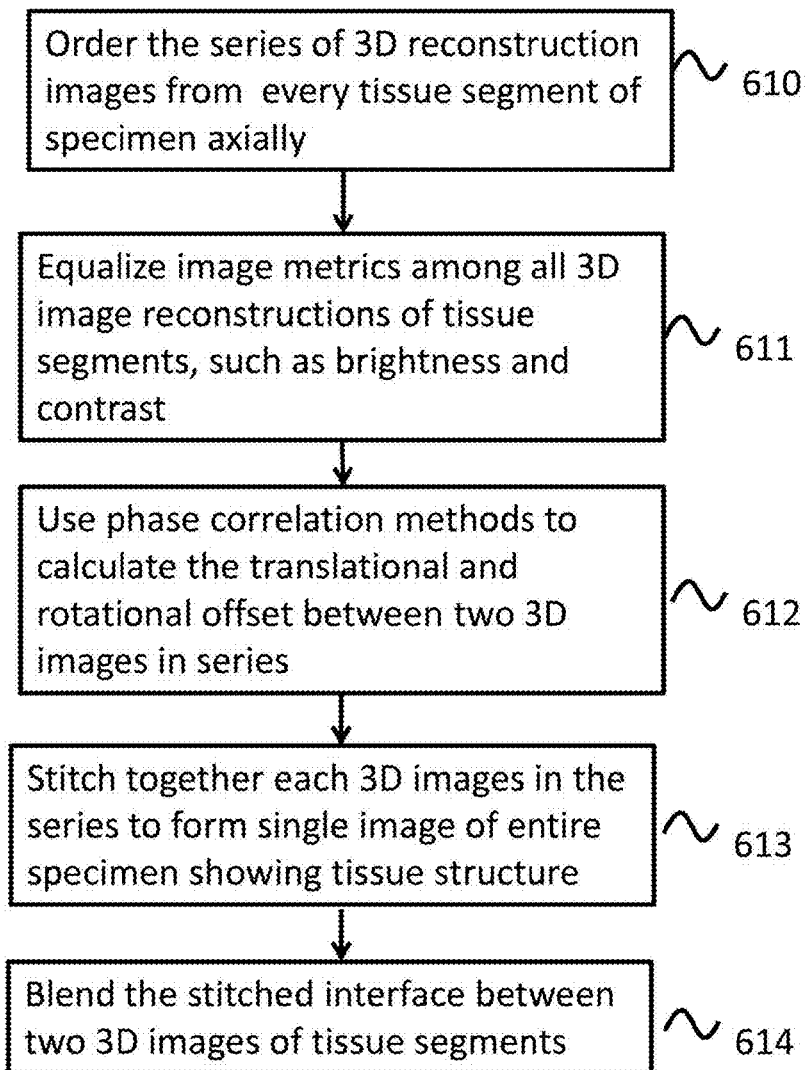
FIG. 10B schematically shows an example of a flow chart for the process of generating a single contiguous 3D image of the specimen using image stitching and blending techniques.

FIG. 10B shows a flow diagram for the process 616 of generating a single contiguous 3D image of the specimen using image stitching and blending techniques. During imaging, different parts of the tissue are moved into field of view by translational stage. There is overlapping area between each set of projection images. Each set of projections is reconstructed individually. All the 3D segments will be put into order axially at step 610. Then all the image metrics, such as brightness and contrast are equalized at step 611. Phase correlation methods can calculate the translational and rotational offset between two 3D images at step 612. After these offsets are determined, these 3D images can be stitched together for whole tissue visualization at step 613. After stitching, blending is applied to adjust light intensity differences between images and minimize the visibility of seams between images at step 614.

Figure 11A:
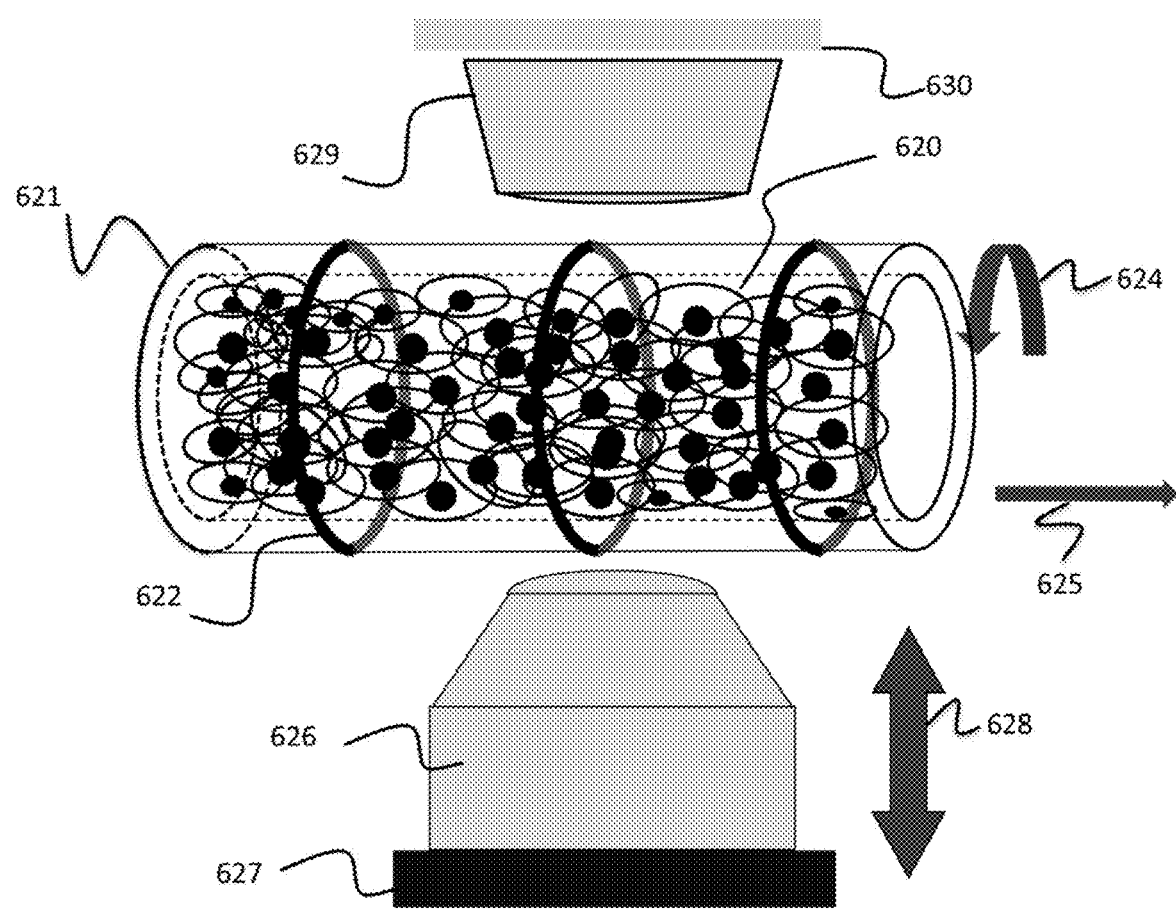
FIG. 11A schematically shows a diagram of the microscopic imaging field of the optical imaging method with close-up side view of a section of the TNCB specimen in a transparent tube with axial registration markings.

FIG. 11A shows the OPTM instrument with close-up view of a section of TNCB specimen 620 in tube 621 with axial registration markings 622. Mechanical vibrations of tube during rotation may cause misalignment of projection images. Registration rings 622 are drawn on the outside of tube 621 for image registration. These rings can be formed by depositing ink using some common nanofabrication techniques. For example, a stamp with line pattern can be produced. The template for the stamp can be produced by photolithography techniques. The photomask can be made on a laser mask writer. Photoresist is applied to a photomask with line pattern. The desired distance of rings on the tube determines the distance between two lines. Then the photoresist is exposed to UV light. The pattern will appear after the photoresist is developed and washed. The template is then placed in a Petri dish and mixture of PDMS prepolymer and curing agent is poured onto the template. After being cured at high temperature, PDMS can be peeled off to serve as a stamp. Dye can be applied to the surface of the stamp then roll the tube on the stamp so that the ring pattern can be produced on the outer surface of the tube. The distance between two rings depends on the system setup, such as objective lens used, camera chip size, etc., and there should be at least one ring appearing within the field of view. For example, if the system setup is this: a tube with a diameter of 250 μm, a camera chip with a size of 1600×1200 pixels (pixel size 7.4×7.4 μm), and a 40× objective lens, the interval should be about 150 μm. The width of the ring should be about several microns so that its shadow won't affect the projection images. After taking all the projection images, all the images are aligned so that the same dark ring appears in the same position on all images. Condenser lens 629 provides illumination for absorption images. Filters 630 may be put in the light path to enhance the image contrast. For example, for hematoxylin stained sample bandpass filter with center wavelength of 580 nm may be used since the absorption peak of hematoxylin is around 580 nm. If the system is working in multi modes, filter 630 should be chosen so that it won't affect the signal in other modes. For example, in absorption and fluorescence dual modes, the light that filter 630 passes should avoid the excitation wavelength range for the fluorophores used in the fluorescence mode. Scanning can be performed in two different ways. Tissue is moved into field of view by translational stage and then kept stationary while motor rotates the tube to take projection images. The second method is to continuously translate the tube while motor rotates the tube in a synchronized manner. The objective lens 626 sits on PZT scanner 627. MIPOS 500 scanner from Piezosystem Jena can scan over 400 μm, which is suitable for the tissue biopsy imaging. The focal plane of the objective lens is scanned 628 through the sample to take one projection image. Computer controls the synchronized movements of PZT, rotation motor and translational stages. The computer is connected to the PZT controller by RS232 line. The controller can also receive feedback signal from the PZT and monitor the position information of PZT. FIG. 10A shows the PZT can work in two different modes: one is continuous scanning; the other is step by step. For continuous scanning, the PZT can be driven by a sinusoidal wave or triangular wave. Sinusoidal wave may provide faster scanning speed, but the path is not very linear. Triangular wave can provide more linear movement, but scanning speed may be limited. The maximum scanning range of the PZT also shrinks as the scanning frequency goes up. Since the PZT has a limited frequency response, the response for a triangular wave may have phase delay and also distortion during the turning point of the triangular driven signal. As a result, only the middle part of the response curve can be used, during which the camera captures the projection image. Due to the nonlinear response, this middle part should be large enough to cover the whole specimen, which means the actual scanning range is longer than the specimen size. At the same time, the scanning frequency limits the maximum scanning range of the PZT. There is a compromise between the specimen size and scanning speed. For step-by-step scanning, staircase function can be applied to the PZT. At each position, the camera will capture one 2D image. After a full sequence of 2D images, the projection images are generated by adding all the 2D images in this sequence. Since the scanning speed in this case is very slow, the maximum scanning range can be used. An alternative scanning method may be used to achieve fast scanning and large scanning range simultaneously (*Optics Express*, Vol. 16, 21843). The focus of the objective can be scanned by a mirror that is on the image plane conjugate to the focal plane of the objective. Since the mirror has less mass, it can be scanned much faster. The scanning range of the objective is equal to the scanning range of the mirror times magnification, which can produce large enough scanning range for large tissue specimen.

FIG. 11B shows a close-up view of the specimen. Tissue sample 620 is shown within a tube that can rotate and translate for taking twisted projection images. The region between two coverslips 635 contains index-matching medium 637 such as optical gel or immersion oil, which surrounds the tube and has refractive index n3. The refractive index differences between tube 621 (n1), cleared tissue 620 (n2) and refractive index matching medium 637 (n3) should be as small as possible to reduce the aberrations. The material of tube 621 can be plastic, glass, etc. The choice of the material also depends on the properties of the signal from the specimen. The material should have the maximum transmission in the wavelength range in which the signal lies.

Figure 12A:
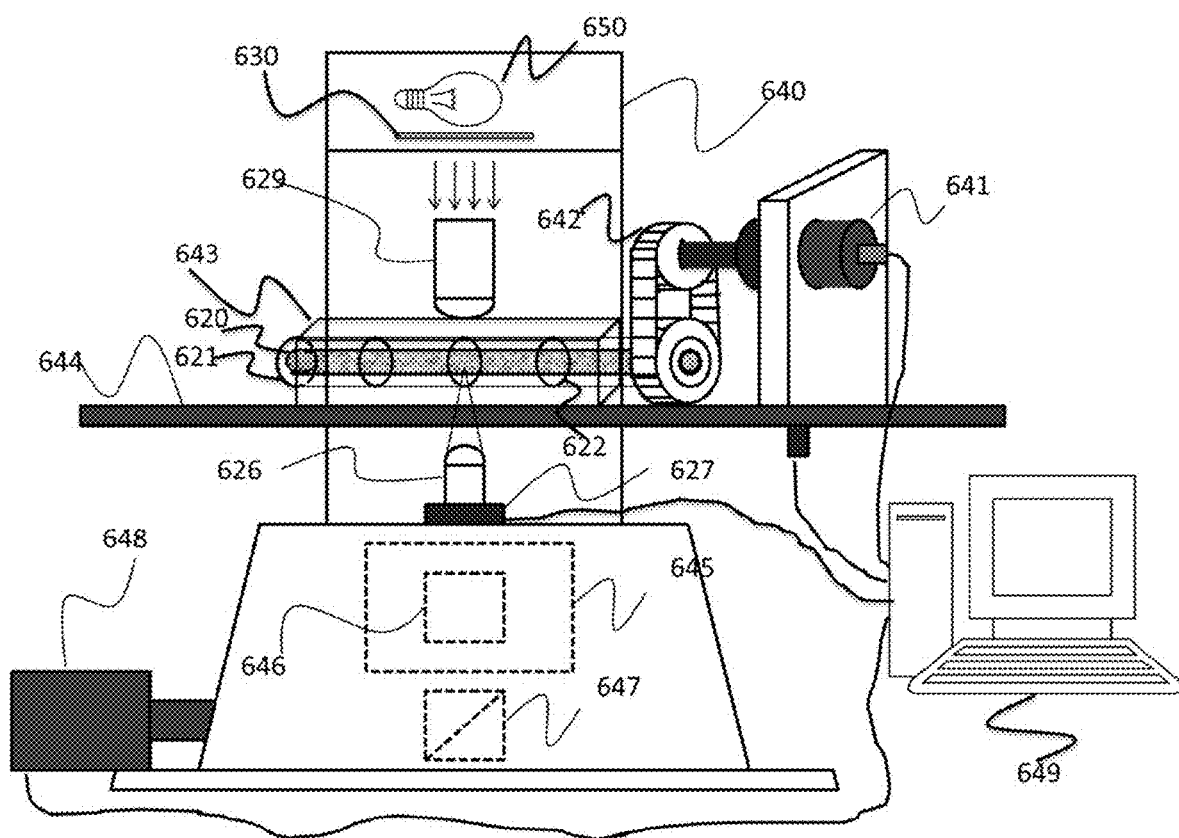
FIG. 12A schematically shows a diagram of the optical imaging instrument with TNCB specimen in tube being scanned using the method of 3D imaging a series of segments of tissue specimen.

FIG. 12A shows the entire setup of the OPTM system. Tissue 620 is cleared, stained and then inserted inside tube 621. Tube 621 is held inside transparent chamber 643, which is filled with refractive index matching medium. There are registration rings 622 on the outside of tube 621 for image registration. Motor 641 and tube 621 are connected through a series of gears 642. Motor 641 rotates tube 621 for taking projection images from different perspectives. Translational stage 644 can move the tube relative to objective lens 626 so that different part of tissue 620 can be imaged and then stitched together for visualization later. Tissue sample 620 can be imaged in both absorption and fluorescence mode. Transmission illumination 640 is provided by HTQ lamp 650. Filter 630 may be added in the transmission illumination path to enhance the contrast. A mercury lamp provides fluorescence illumination 645. A shutter may be inserted before the mercury lamp to reduce photobleaching rate. The shutter can block the excitation light between the exposure times so that unnecessary excitation of the fluorophores inside specimen can be avoided. Filter cube 646 in the light path can be used to extract other types of signal, such as fluorescence, different polarized light. Filter cube 646 for fluorescence is composed of three filters: excitation filter, emission filter and dichroic filter. The excitation filter only transmits light having a wavelength band necessary to excite fluorophores inside the specimen or the specimen itself. The dichroic filter reflects the excitation light to the specimen and transmits fluorescence light emitted from the specimen. The fluorescence then passes the emission filter and is reflected by mirror tube 647 to camera 648. If polarization mode is used, excitation filter and emission filter are changed to two polarizers, which have orthogonal transmission axes. Objective lens 626 sits on PZT scanner 627, which scans the focal plane of the objective through the specimen to generate one projection image. The scanning range of PZT 627 should be chosen so that it can cover the whole tube. The camera chip size should be chosen so that the system satisfies Nyquist criterion. Camera 648 can be monochrome or color camera. For example, the specimen is stained with hematoxylin and eosin, color camera may be used for two color absorption imaging, since signals from two different dyes can be captured simultaneously so that registration error can be avoided. Computer 649 controls motor 641, translation stage 644, PZT scanner 627, and camera 648.

Figure 12B:
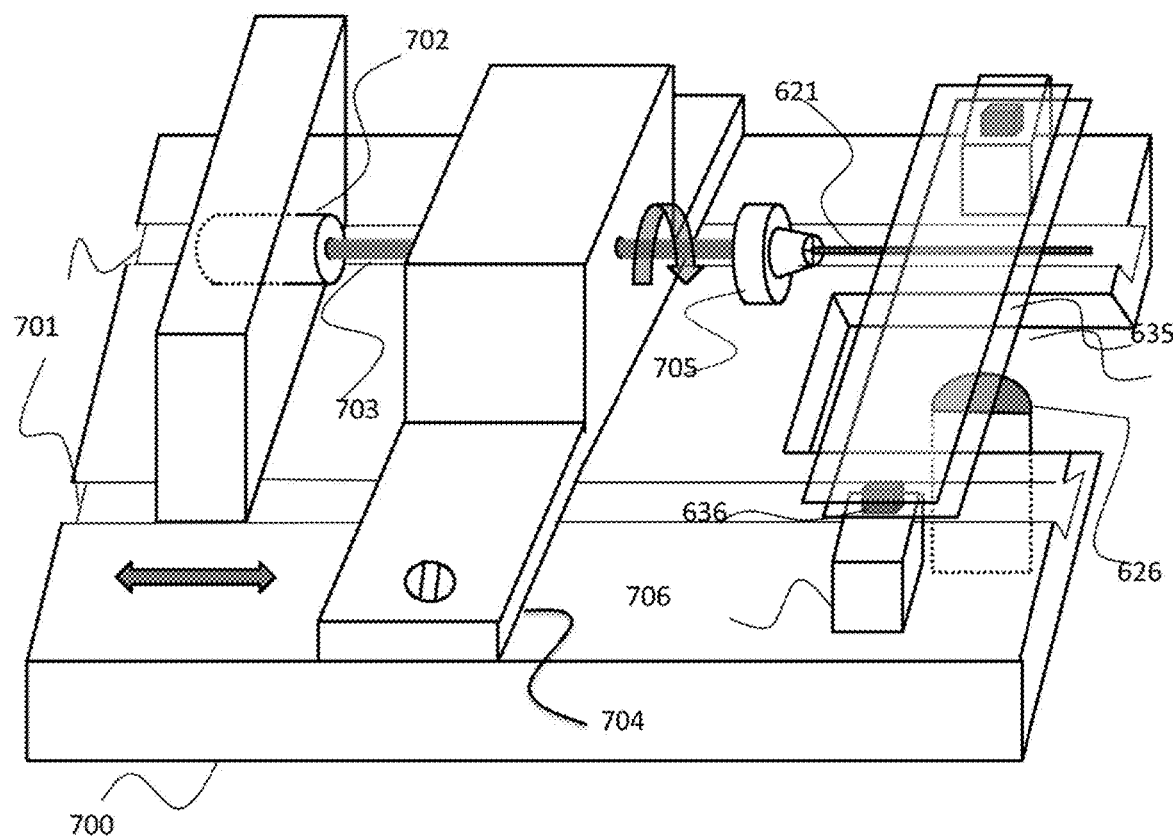
FIG. 12B schematically shows a diagram of the optical imaging instrument stage with TNCB specimen in tube being scanned using an angled, curved, or twisted pathway about the entire tissue specimen.

FIG. 12B shows the setup of the entire TNCB specimen being scanned using one continuous twisted scan path. There are two sliding tracks 701 on stage 700, on which motor 702 can move linearly. Lead screw 703 is attached to motor 702 coaxially. Lead screw 703 passes through a lead nut, which tight fits into iron block 704 that is fixed on stage 700. Drill chuck 705 is attached at the end of lead screw 703. Tube 621 with tissue specimen is held by drill chuck 705. When motor 702 rotates, lead screw 703 translates the rotation motion into linear motion. Lead screw 703 leads tube 621 to rotate and move simultaneously. The ratio between rotation speed and linear movement speed can be controlled by the screw threads. Tube 621 is immersed in refractive index matching medium between two coverslips 635 or can be held inside a chamber filled with refractive index matching medium.

Reconstruction

Reconstruction can be performed by two main methods depending on how the projection images are acquired. The first, described significantly above, moves a segment of the sample into the field of view, projection images are acquired from various angles around the object, and the segment is reconstructed using methods such as filtered backprojection. A new segment of the sample is moved into the field of view where there is some overlap with the previous segment and reconstruction is performed for this segment. This procedure is performed for every desired segment and the final composite image is constructed by stitching the segments together. An alternative method, which is similar to Helical CT, continuously moves the sample past the source and detector. This method of acquisition is described below and two main means of reconstructing this data set is presented.

Helical Reconstruction

Figure 13A:
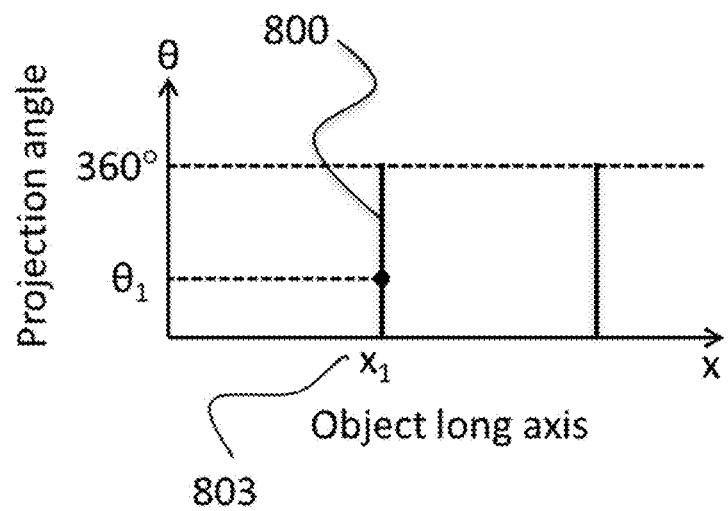
FIG. 13A schematically depicts data acquired during sequential CT and the data required to reproduce a single slice ($x_1$). For traditional CT, the data acquired is in the same plane as the data required to reconstruct the plane.
Figure 13B:
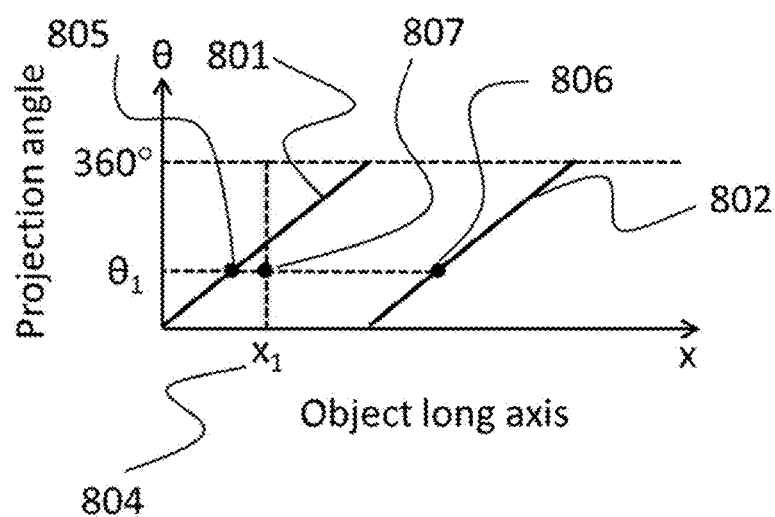
FIG. 13B schematically depicts data acquired during helical CT and the data required to reproduce a single slice ($x_1$). For helical CT, data is acquired on an angle with the object's long axis and multiple slices are interpolated to get data on a single plane.

FIGS. 13A and 13B show a comparison of data acquired between sequential CT 800 and helical CT 801 and the data required to reproduce a single slice 802 and 803 ($x_1$) for each method, respectively. θ is the angle of the projection and x is the location along the object. If volumetric data is desired, it was originally acquired slice by slice using traditional CT schematically depicted in FIG. 13A. However, acquisition is inherently slow and mechanical errors, resulting from the stopping and starting motion of moving the object past the source and detector, reduce the resolution in the direction of object motion. Helical CT was developed to improve acquisition time whereby projection images are collected as both the X-ray source/detector rotate around the object of interest and as the object of interest continuously moves past the source/detector, schematically depicted in FIG. 13B. The continuous movement allows for increased acquisition speed and reduction in mechanical errors (since continuous movement provides greater stability as compared to the stop/start motion). The two methods are compared below. For traditional CT, data 800 acquired is in the same plane as reconstruction plane 803. For helical CT, data 801 is acquired on an angle with the object's long axis and multiple slices are interpolated to get single plane data 802. For example, if dots 805 and 806 are acquired on slices 801 and 802 then these points are interpolated to get point 807 on slice $x_1$. This interpolation process is repeated for all projections. These single plane datasets are then reconstructed using similar methods as sequential CT. 2D images are reconstructed from projection images using the filtered backprojection, inverse Radon transform, or some variation thereof. Reconstruction algorithms have been developed for various source/detector geometries, such as fan-beam or cone-beam. Cone-beam methods employ 3D reconstruction algorithms.

Figure 13C:
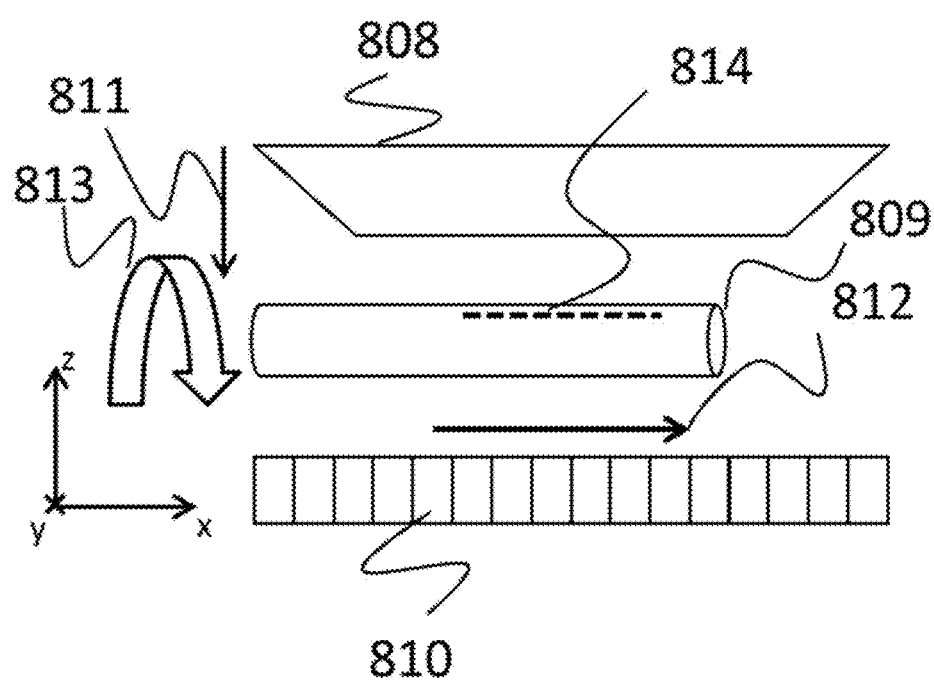
FIG. 13C illustrates a single camera exposure where the focal plane is scanned through the transparent tube, while the tube is simultaneously moving forward. The objective is illustrated as a trapezoid and the distance between the objective and the focal plane is constant (or the focal distance). The boxes at the bottom of the figure represent a row of stationary detector channels (or pixels in a camera).

FIG. 13C shows a single exposure where objective 808 scans down simultaneously as object/tube 809 moves forward. The signal detected at each pixel 810 (where the pixels are exaggerated in size compared to the object of interest) is not a single vertical plane, but an arc based on objective scanning velocity 811, object movement velocity 812, and camera/pixel 810 exposure time. The x-axis is defined as direction of transparent tube translation 812, the z-axis is direction of objective scanning 811, and the transparent tube continues to rotate 813 in the y-z plane as before. This method of acquisition is much different than traditional X-ray based spiral CT where the X-ray pulse is of such short duration and fast velocity that the objective of interest effectively does not move in the direction of 812 during acquisition of each projection. Therefore, each projection image can be assumed to be of a single plane of the object. However, in the case of the OPTM where projection images are produced by optically integrating or electronically summing different focal planes 814 through a means of mechanically moving either the objective, transparent tube 809, or a mirror (to alter the point spread function) this assumption is no longer valid. In this case, projections are built over a relatively slow time frame (milliseconds) as the object translates past the detector.

2D Data Acquisition

In order to better understand how the data is acquired helically and reconstructed in 3D, reconstruction along curved paths is first discussed in 2D. In this case, both the focal plane moves in the z-direction and the object rotates in the y-z plane.

Figure 13D:
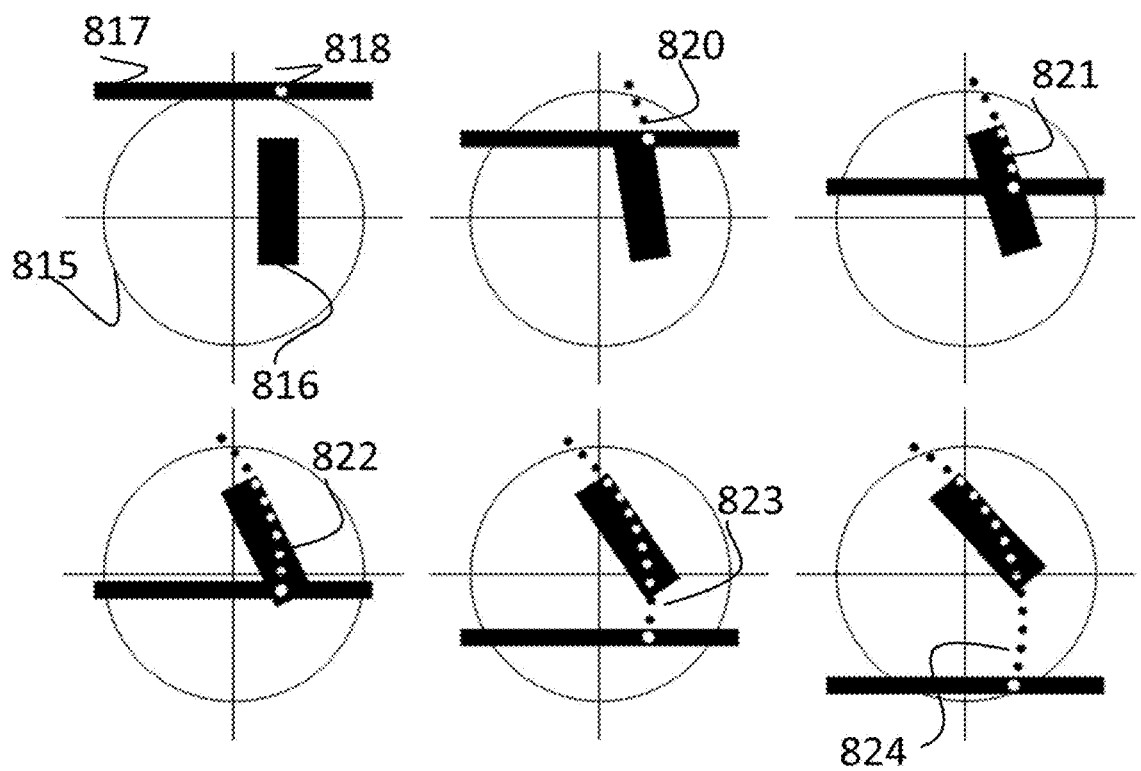
FIG. 13D shows an example of curved scan path kinematics where the object of interest is simultaneously moving as the focal plane scans.

FIG. 13D illustrates the idea of building a projection for a single pixel based on an arc. This idea is referred to as the scan path kinematics. The figure shows how projections are built over successive time increments (in the OPTM projections are actually built continuously over the entire camera exposure). Circle 815 indicates a cross section of the sample (or boundary of transparent tube 809) and rectangle 816 represents an object within the sample. In the case of the OPTM, transparent tube 809/815 would be filled with a tissue sample. Horizontal bar 817 on top of circle 815 represents the focal plane and white dot 818 indicates a representative location in focal plane 817 corresponding to a particular pixel location. With each time increment, focal plane 817 descends while sample 816 rotates counterclockwise about the origin of the coordinate axes. Trail of dots 820, 821, 822, 823, 824 indicates the location in the tissue sampled at successive times. Dots 819 are shaded to contrast with the background and the configuration is illustrated for every 4th time interval.

Figure 13E:
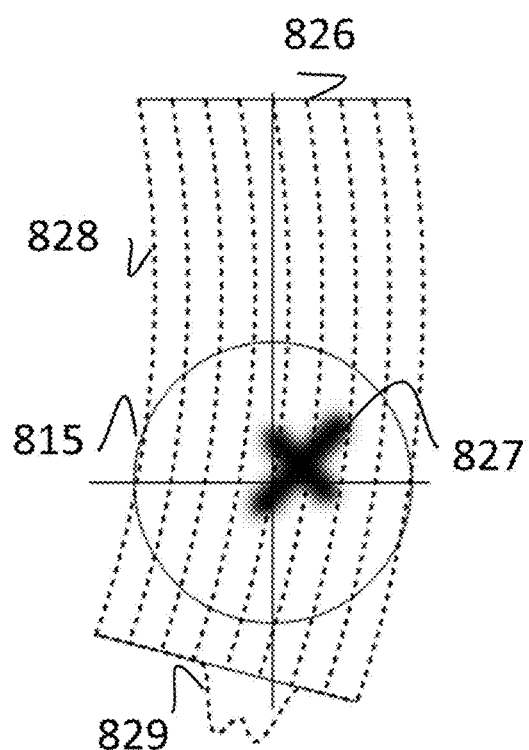
FIG. 13E illustrates curved paths produced by the scan path kinematics and the projection images produced for two different orientations of the object of interest.
Figure 13F:
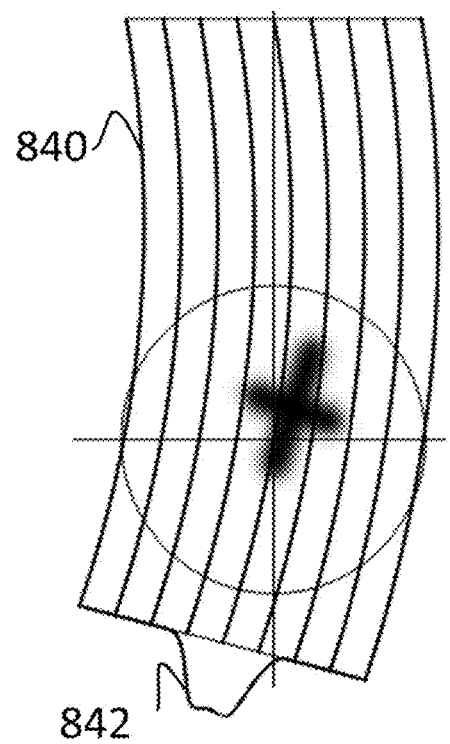
FIG. 13F illustrates curved paths produced by the scan path kinematics and the projection images produced for a different orientation of the same object of interest in FIG. 13E.

FIG. 13E illustrates that the entire focal plane 826 corresponds to a row of pixels 810 where object of interest 827 located in the transparent tube 815. Initial projection paths 828 are presented by dotted arcs and projection 829 is built as focal plane 826 moves and object 827 rotates. Projection 829 is just a summation of the intensity of the object 827 through path 828. Projection paths 840 are produced at another time point and its projection 842 is shown at the end of the arcs of FIG. 13F. Notice that projections 829 and 842 have different heights because projection paths 828 and 840 go through different amounts of object 827. By collecting many projections from various angles around the object 827, the object is able to be reconstructed.

Backprojection Reconstruction

The most straightforward means to reconstruct the data is with the traditional backprojection technique. Used normally for straight-line paths, this method basically smears projection intensities over the reconstruction grid at the angle that the projection was acquired. Since the projection data will often not directly align with the reconstruction grid, some means of interpolation is used to determine the appropriate intensity for each pixel. This process is repeated for every projection image and the final reconstruction is a summation of all the smeared projection images. Many modifications have been introduced over the years to this method, including most notably the filtered backprojection. Backprojection inherently enhances low frequency content, so different filters, such as the ramp filter, have been used to reduce the low frequency content. The filtered backprojection theory relies on the projection-slice theorem and Fourier transforms to reconstruct and filter the projection data.

The OPTM could use similar ideas to reconstruct the image only it would not smear the projection at a single angle, but instead it would follow the path described by the scanner path. Filters could also be added to the reconstruction process in order to reduce the low frequency content; however, the filters would require different implementation since the projections are acquired on curved paths.

Figure 13G:
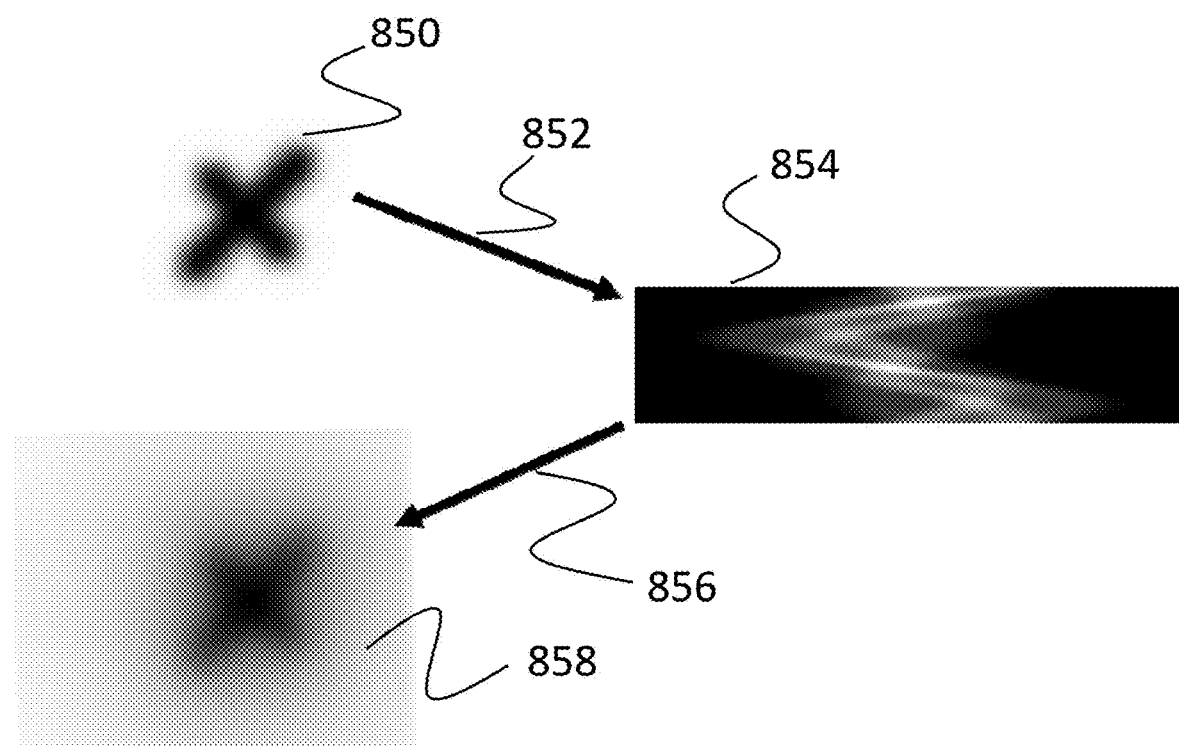
FIG. 13G shows an example reconstruction using the twisted back projection without any filtering. Projection images of the original object are produced using a simulated Twisted Radon transform to produce a sinogram, where the horizontal axis is the location along the projection and the vertical axis is the starting angle of the scan kinematics. From this data, the image is reconstructed using backprojection taking into account the scan kinematics.

FIG. 13G provides an example two-dimensional simulation of projection 852 and backprojection method 856 on curved paths (i.e. 828). Projection data 854 is acquired from the original object 850 based on curved paths and shown as sinogram 854, which is an image of location along detector (horizontal axis) versus starting angle of the projection (vertical axis). This procedure is termed Twisted Radon Transform. From sinogram 854, original object 850 is reconstructed using backprojection 856 without any filtering. As shown, original object 850 is fairly well reconstructed in 858, although low frequency content is certainly enhanced. Filters could be employed to enhance the reconstruction.

Figure 13H:
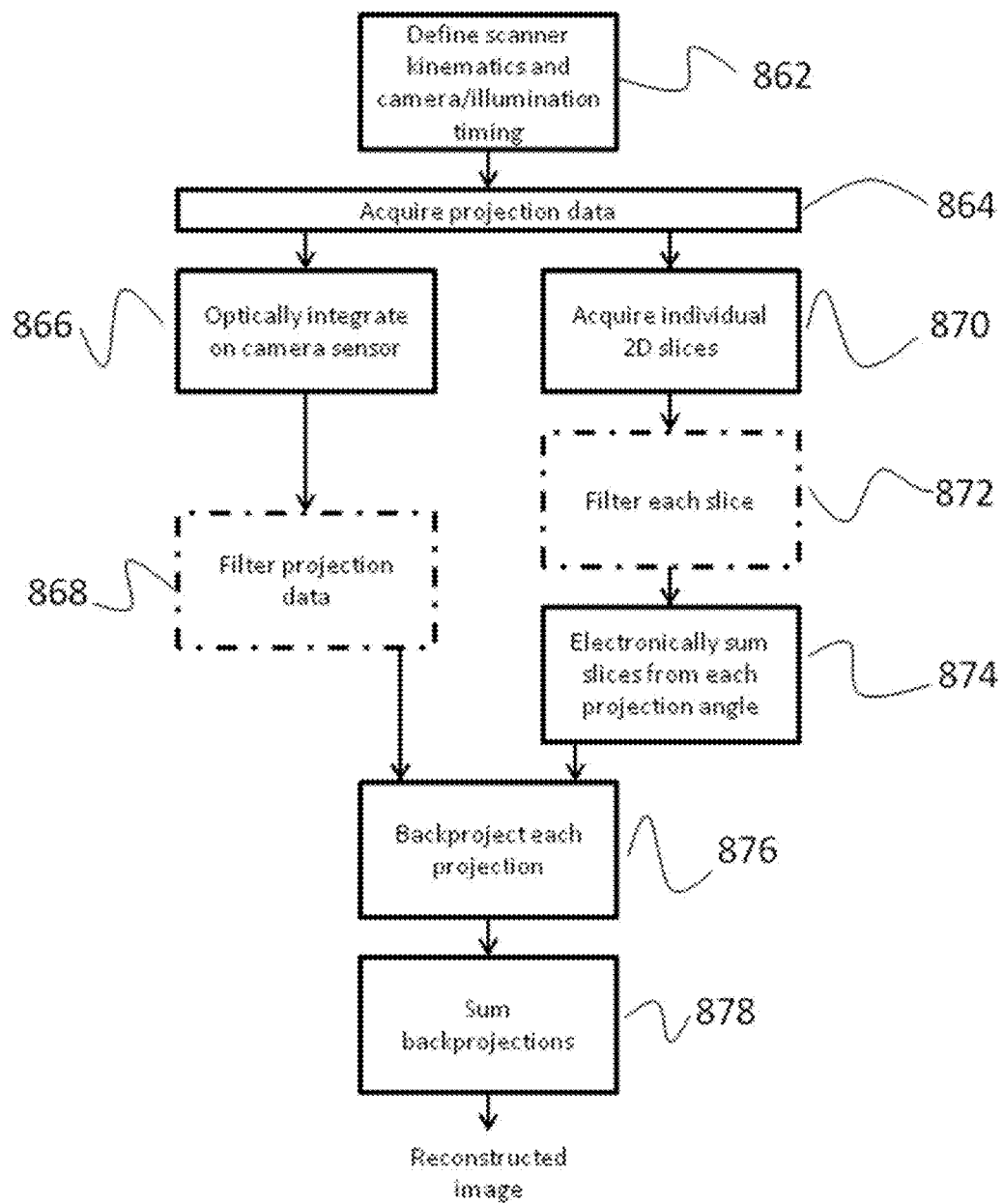
FIG. 13H is a flow chart of the two-dimensional back-projection reconstruction where projection images can be acquired by either optically integrating or electronically summing. Filtering is also included as optional steps.

FIG. 13H shows the entire two-dimensional reconstruction for backprojection method based on curved paths (i.e. 828) for either optically integrating the focal planes or electronically summing images acquired at different axial locations. Scanner kinematics 862 must be determined based on objective scan velocity 811 and transparent tube velocity 812. These velocities are important to know scan paths (i.e. 828), which are important to smear the projection data over the reconstruction grid. Projection data can now be acquired by 864, either optically integrating in step 866 or electronically summing 870 for all desired rotations around the object of interest. Following optical integration in step 866 there is an optional step of filtering the projection data 868. This filtering would reduce the low frequency content of the projections to produce better reconstructions. If instead individual 2D slices were acquired 870, these images could be optionally filtered in step 872 to reduce the low frequency content and/or deconvolved with the point spread function to remove blurring inherent in the imaging system. In step 874, the filtered or unfiltered images would be summed electronically. This summation procedure could be performed after accounting for image location, so as to remove the curved acquisition path. Whether optically integrated or electronically summed, each projection can now be reconstructed in step 876 by smearing the data or using the projection-slice theorem. All the backprojections can be summed in step 878 to produce a reconstructed image.

Algebraic Reconstruction Technique

The Algebraic Reconstruction Technique (ART) is presented as an alternative method to reconstruct an image of the scanned object from the data acquired from the OPTM. The main difference between this method and the backprojection technique is that instead of smearing the projections on the reconstruction grid, the reconstruction intensities are directly solved by setting up a large linear algebra problem relating known scan path kinematics, known projection intensities, and unknown reconstruction intensities. This technique will be described in two dimensions as a means to reconstruct from data acquired along curved paths. The problem is readily extended to three dimensions and the associated modifications will be described in a later section.

Figure 14A:
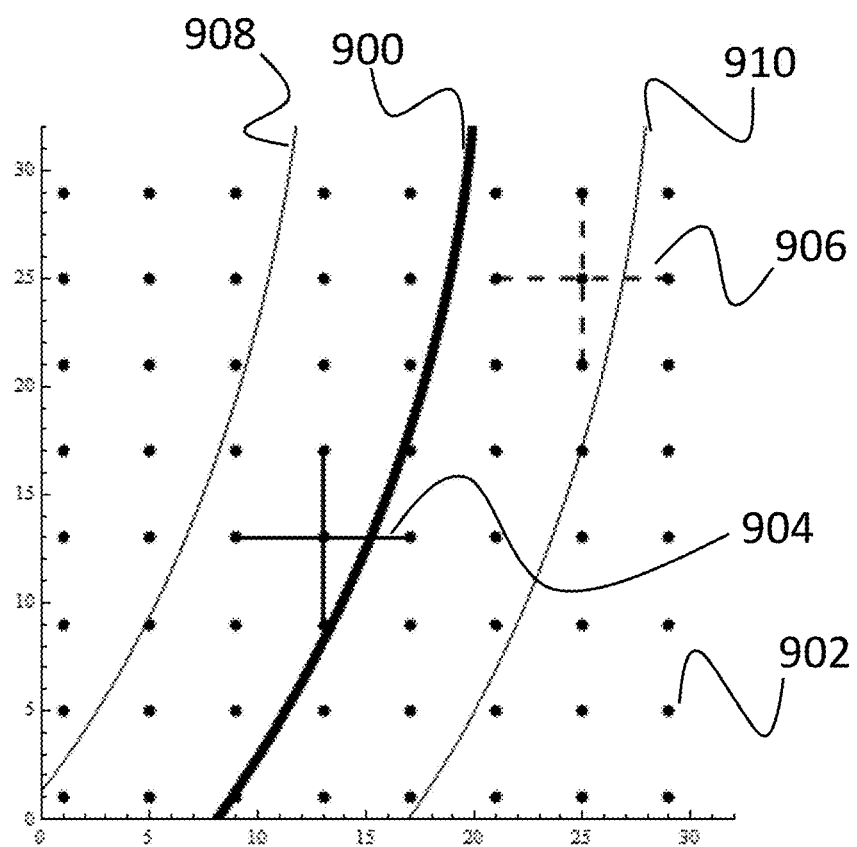
FIG. 14A illustrates the Algebraic Reconstruction Technique (ART) with an example scan path and the pixels required to compute interpolation coefficients necessary for reconstruction.

ART has been used in CT and other fields; however, the main difference between those applications and this one is that the paths are curved rather than straight lines. Since the OPTM includes control of objective scan velocity 811, transparent tube rotation velocity 813, and tissue translation velocity 812, the scan path kinematics can be explicitly defined. These kinematics are used to derive equations that implicitly describe the scan path used to acquire each pixel in every projection image. As shown in FIG. 14A, dark black line 900 (which represents the scan path) is not directly in line with Cartesian grid pixels 902. The reconstruction problem is really to determine how unknown pixel intensities 902 relate to the known scan paths 900 and known projection intensities (i.e. 829). Unknown pixel values 902 will often be referred to as reconstruction pixels.

ART involves formulating and solving a system of linear equations involving reconstruction pixel values 902 and the known projection intensities (i.e. 829). Each equation expresses a known projection value along a scan path (i.e. 900) as a linear combination of reconstruction pixel values 902. Assembling the linear equations produces a linear algebra problem where the matrix of coefficients multiplies the vector of unknown reconstruction pixels to produce the known vector of projection intensities. The coefficients in the matrix account for how each reconstruction pixel 902 contributes to each path projection intensity. The coefficients can be approximated by employing an interpolant of the reconstruction intensity function (defined across the continuous scan domain) and computing the integral of the interpolated reconstruction intensity function along the parametrically defined scan paths. However, such an approach requires splitting the integration up into a multiplicity of subintegrals corresponding to each region where the interpolant has a particular analytic form (e.g. for the simplest piecewise constant approximation of the reconstructed intensity function, a separate integral must be computed for each pixel traversed by the scan path along with corresponding limits of integration that must also be determined).

Our preferred implementation instead employs an implicit description of the path and wavelets to approximate the continuously defined functions based on their pixel values. The implicit description of the path is comprised of a path function that depends on the spatial coordinates, has value zero on the path, and changes sign as the path is crossed transversely. After evaluating the path function at each pixel, we express the implicit path description as a combination of the path pixel values and the wavelet approximant. Thus all the information for computing the intensity integral along the scan path (i.e. 900) is localized onto the pixel grid 902, and the intensity integral along the scan path is evaluated using the multiresolution approximation [Resnikoff and Wells, 1998, pp. 273-279]:

$$J = -\frac{1}{2}\sum_{i,j} I_{i,j} C_{i,j} \quad (1)$$

$$C_{i,j} = \frac{\left(\left(\frac{\partial}{\partial x}\text{sgn}(f)\right)_{ij}\left(\frac{\partial f}{\partial x}\right)_{ij} + \left(\frac{\partial}{\partial y}\text{sgn}(f)\right)_{ij}\left(\frac{\partial f}{\partial y}\right)_{ij}\right)}{\sqrt{\left(\frac{\partial f}{\partial x}\right)_{ij}^2 + \left(\frac{\partial f}{\partial y}\right)_{ij}^2}} \quad (2)$$

where J is the vector of known projection pixel values, $I_{i,j}$ is the vector of unknown pixel intensities, $C_{i,j}$ is the coefficient matrix determined from implicit scan path functions, $f$ is the implicit scan path function, and sgn( ) is the signum function.

Once specific device kinematics 912 are chosen (FIG. 14B), Equation 2 specifies a one-time calculation of the ART coefficient matrix 914 that can be pre-computed based on specific device kinematics. Note that Equation 2 arises by invoking the Divergence Theorem to express the intensity integral along the scan path to an area integral involving the inner product of the normal to the path with the gradient distribution of the support function for the region on one side of the scan path. The support function is expressed in terms of the signum function acting on the path function, and derivatives in Equation 1 are evaluated via a useful property of wavelets: for a given wavelet (e.g. Daubechies wavelets of a specified order), there is an associated finite vector of connection coefficients and the derivative of the wavelet function at a point can be evaluated by convolution of the pixel data with the vector of connection coefficients.

In geometric terms, there is a known mask or template that can be applied specifying a linear combination of the local pixel values to produce the pixel value for the derivative. As a simple example, the lowest order Daubechies wavelet (also known as the Haar Wavelet) has the associated connection coefficient vector $\{-\frac{1}{2}, 0, \frac{1}{2}\}$, which produces the equivalent of a standard central difference estimator of the derivative:

$$\left[\frac{\partial f}{\partial x}\right]_{i,j} = \frac{(f_{i+1,j} - f_{i-1,j})}{2\Delta} \quad (3)$$

In geometric terms, this means that only nearest neighbor pixels contribute to the derivative, so when derivatives in both the x and y directions are accounted for (since both derivatives appear in Equation 1), the derivative mask has the shape of a cross with coefficient values $+\frac{1}{2}$ on the right and top, $-\frac{1}{2}$ at the left and bottom, and zero at the center. FIG. 14A illustrates a grid of pixel locations, scan path 900, and cross 904 and 906 that represent the Haar derivative masks for the points at the center of each cross. Since the numerator of Equation 2 includes the derivatives of sgn($f$) which vanish unless $f$ changes sign (and such sign changes occur on the scan path), pixels can only contribute to the integral if their derivative mask lies across the scan path, as is the case for 904. On the other hand, derivative mask 906 does not cross the scan path, so it does not contribute to the integral. Lighter curves 908 and 910 illustrate approximate boundaries of the region where pixels can contribute to the intensity integral along the scan path shown. The contribution to the intensity integral along the scan path vanishes for all pixels outside of this neighborhood of the scan path. Thus many of the coefficients are zero, and the ART coefficient matrix tends to be sparse. (Note that computation of smoother reconstructed intensity functions involves wavelets of higher order, which have longer vectors of connection coefficients [Resnikoff and Wells, 1998, Ch. 10]. The length in pixels of the crosses for the corresponding derivative masks increases but remains small compared to the pixel width of the scan domain so that the ART coefficient matrix remains sparse).

Figure 14B:
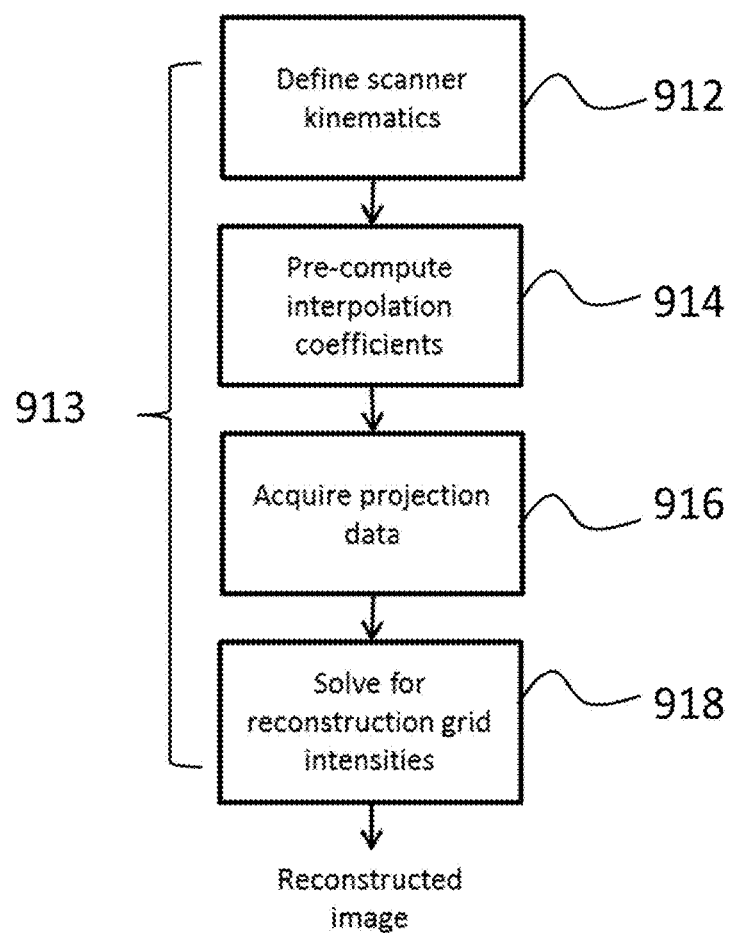
FIG. 14B shows the flowchart to reconstruct projection images using the Alternative Algebraic Reconstruction Technique (ART).

Having now specified the formulation of the ART problem (which is shown in FIG. 14B as a flow diagram), what remains is to solve the linear algebra problem in step 916 after data acquisition in step 918, which can be done using standard techniques for solving sparse linear algebra problems. Our preferred embodiment employs the inherent multiresolution nature of wavelet approximants to initially solve smaller downsampled versions of the ART problem, which are then upsampled to provide starting values for iterative solution of the ART problem at full resolution following similar developments for numerical solution of large linear systems arising from discretization of partial differential equations [Diaz, 1999].

3D Acquisition

Now we expand this idea of collecting projections based on arcs to 3D where the object is now moved past the source and detector. Unlike traditional CT, we have the advantage of a large 2D detector (such as a CCD) compared to the object of interest. This detector allows us to acquire projection images in parallel for every desired initial angle of rotation while the sample is in the field of view (FOV). Angle θ is used to describe the angle the tissue sample makes with the y-z axes. Refer to FIG. 13C for better illustration of the problem where the transparent tube 809 is moving past the objective 808 and detector 810.

Figure 15A:
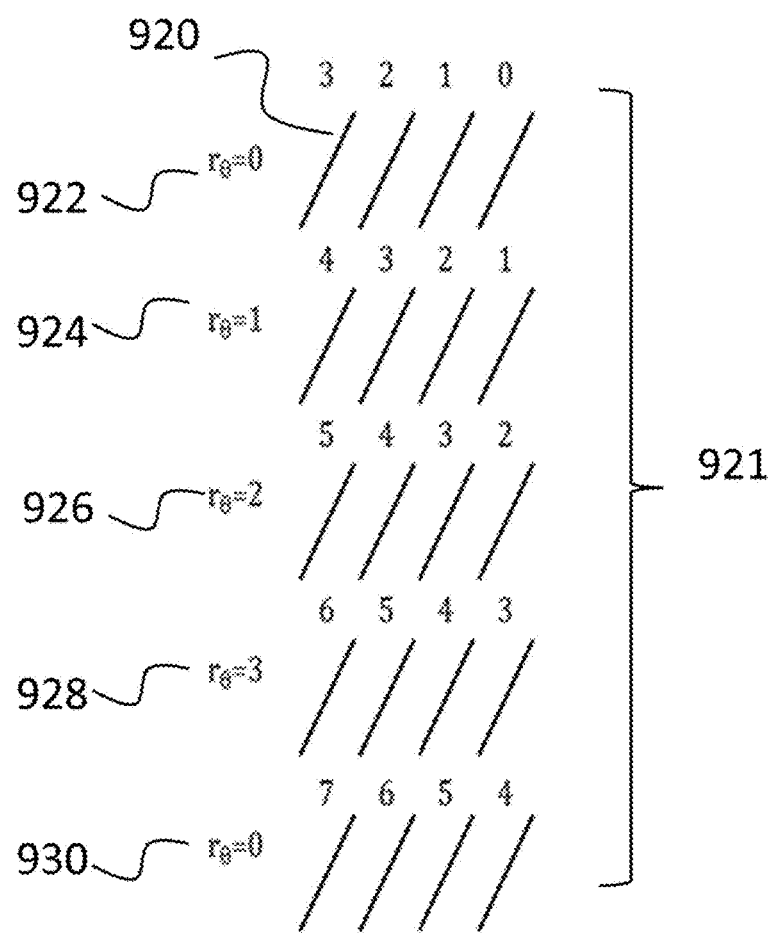
FIG. 15A shows how different scan paths can be acquired in parallel as the object translates past the source and detector through the field of view.

FIG. 15A describes the parallel acquisition 921 of each desired arc (i.e. 920) where each arc is most likely out of order depending on when the tissue sample enters the FOV. For ease of description, four desired rotations ($r_\theta$; i.e. 922) are assumed where transparent tube 809 is constantly rotating to these angles in consecutive order 924, 926, 928, 930. The lines represent the paths of integration (i.e. 828) detected for a single row of pixels (represented as only 4 pixels) in the FOV along the x-axis (axis of transparent tube translation). The first image, acquired at $r_\theta$=0, contains arcs of integration 3-2-1-0. After the fourth rotation, all four desired rotations have been acquired for arc 3. However, arc 4 enters the FOV at $r_\theta$=1 and $r_\theta$=0 isn't acquired until it is exiting the FOV. If reconstruction is performed using backprojection then each projection can be backprojected as soon as that particular image is acquired. The resulting single angle backprojection images can be assimilated as they are acquired to reconstruct a single backprojected image. However, if reconstruction is performed using ART then the various projection images from the same region of tissue are assimilated as they pass through the field of view. Reconstruction of the specimen can proceed in parallel with the helical data acquisition as the various arcs are obtained from the different regions in the sample. The resulting 3D image is a composite image of the region of interest in the tissue.

Figure 15B:
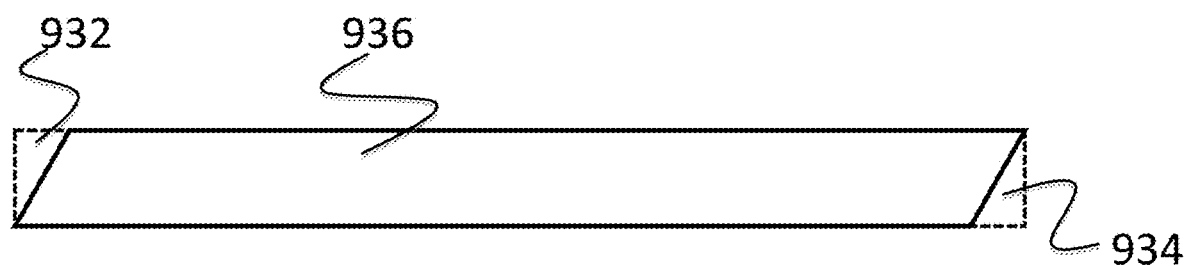
FIG. 15B illustrates the long object problem inherent in helical data acquisition. This problem can be mitigated using previously designed techniques for CT.

FIG. 15B illustrates tube 809 and the simplistic method described above to acquire all the data. The method described ignores tissue at the beginning region 932 and end region 934 where region 936 is the only projection data acquired from the core tissue sample. The amount of data not acquired is dependent on how fast the transparent tube is translated in the x-direction. A similar condition is described as the long object problem in CT. A variety of methods have been developed to acquire this extended data. Similar methods could be employed in the OPTM to acquire the end caps and be able to image the entire tissue sample.

3D Reconstruction

Reconstruction can be expanded to 3D by two methods depending on the velocity of the focal plane compared to the velocity of the tissue in the x-direction. If the focal plane velocity and the tissue movement in the x-direction are linearly coupled then each projection can be considered to lie on a single plane at an angle ϕ with respect to the x and z directions. From these assumptions the problem could be turned into more of a sequential reconstruction whereby 2D reconstruction algorithms can be used to reconstruct individual planes oriented at the angle ϕ. Either the backprojection or ART method of reconstruction could be directly applied. The angular orientation can be subsequently removed through some means of interpolation (e.g. linear).

In the case where the focal plane velocity and the tissue movement are not linearly coupled then the arcs would have to be described parametrically in 3D. While backprojection could be employed along these 3D arcs, this situation would require a fairly complex filtering method to reduce the low frequency content.

Figure 15C:
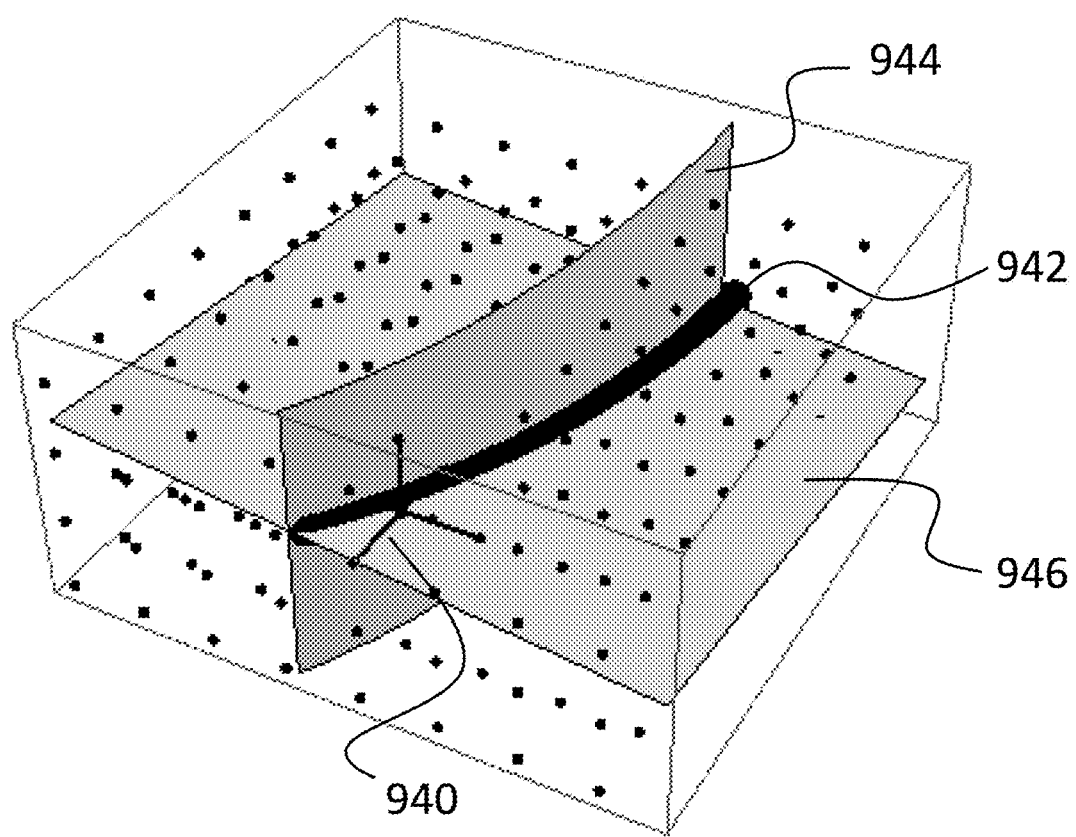
FIG. 15C shows how interpolation coefficients are found for 3D scan paths in ART. Two implicit functions are used to describe the scan path rather than a single three-dimensional polynomial.

Instead FIG. 15C shows how ART directly extends to 3D with minor modifications: the wavelets must be applied along three coordinate directions 940 instead of two; two implicit functions (944 and 946) must be computed so that some subset of their intersection closely approximates scan path 942; computation of the intensity integral along the scan path involves a direct extension of equation 2 to 3D.

Computer Implementation

Both backprojection and ART are highly parallelizable algorithms that can take advantage of either unified or distributed memory based computers or graphics processors. Our preferred embodiment utilizes a Graphics Processing Unit (GPU) because of its unified memory structure and the fact that modern graphics processors contain tens to hundreds of processors that are capable of significantly reducing computation time. The GPUs made by Nvidia have especially desirable qualities in that they can be programmed using Compute Unified Device Architecture (CUDA), which is an extension of the well-known C programming language. CUDA allows for very easy implementation of parallel for loops and summations, among many other programming structures.

The backprojection algorithm is especially well suited to parallelization because each projection angle is smeared back onto the reconstruction grid and then all projection angles are summed at the end of the algorithm. ART is also well suited to parallelization. Computation of the coefficient matrix is completely parallelizable, which we have previously described can be pre-computed based on the scan path kinematics. Solving the linear algebra problem set up by ART could be performed using CULA, which is a combination of CUDA and LAPACK (matrix computation toolbox).

While our preferred embodiment utilizes GPUs, these algorithms can also be implemented on desktops and computer clusters that utilize CPUs as their main processing unit. If written in the C programming language, these algorithms can be parallelized on a single computer using the OpenMP parallel toolbox. Alternatively both algorithms can be written such that they are computed on several computers and information is passed between each one using the Message Passing Interface (MPI) toolbox.

The invention claimed is:

1. A method to prepare a specimen of biological tissue for optical imaging, comprising:
   receiving a thin-needle core biopsy (TNCB) specimen of biological tissue, the TNCB specimen having an elongated shape;
   preserving the elongated shape and integrity of the TNCB specimen during preparation of the TNCB specimen for optical imaging, said preparation including:
      introducing the TNCB specimen into a specimen channel of a microfluidics device, the specimen channel structured to preserve the elongated shape and integrity of the TNCB specimen;
      moving the TNCB specimen from the specimen channel into a specimen chamber of the microfluidics device while retaining the elongated shape and integrity of the TNCB specimen, wherein the specimen chamber is structured to preserve the elongated shape and integrity of the TNCB specimen; and
      preparing the TNCB specimen within the specimen chamber for optical imaging such that the TNCB specimen will retain its elongated shape and integrity during said optical imaging.

2. The method of claim 1, wherein the act of preparing the specimen of biological tissue includes fixing the tissue.

3. The method of claim 1, wherein the act of preparing the specimen of biological tissue includes staining the tissue.

4. The method of claim 1, wherein the act of preparing the specimen of biological tissue includes optically clearing the tissue.

5. The method of claim 1, wherein the act of preparing the specimen of biological tissue includes embedding the tissue.

6. The method of claim 1, comprising:
   after moving the specimen of biological tissue, measuring an optical property of the specimen of biological tissue.

7. The method of claim 6, wherein the optical property is light transmittance.

8. The method of claim 6, wherein the optical property is absorbance at a region of the visible light spectrum.

9. The method of claim 1, wherein the specimen channel and the specimen chamber of the microfluidics device are arranged to receive specimens of biological tissue that are more than 5 mm in length.

10. The method of claim 1, wherein the optical imaging includes optical imaging via a tomographic process.

11. The method of claim 10, wherein the tomographic process is three-dimensional optical projection tomography.

12. The method of claim 1, wherein introducing the TNCB specimen into the specimen channel of the microfluidics device includes introducing the TNCB specimen directly into the specimen channel of the microfluidics device.

13. The method of claim 1, wherein the elongated shaped is defined by a diameter of at least 0.5 millimeters (mm) and a length of at least 5 mm.

14. A method to prepare a specimen for optical imaging, comprising:
   introducing a thin-needle core biopsy (TNCB) tissue specimen into a specimen chamber of a microfluidics device, the specimen chamber having a structure arranged to preserve an elongated shape of the TNCB tissue specimen; and
   while the structure of the specimen chamber maintains the elongated shape of the TNCB tissue specimen:
      applying a fixation solution to the TNCB tissue specimen;
      applying a staining solution to the TNCB tissue specimen; and
      applying an optical clearing solution to the TNCB tissue specimen.

15. The method of claim 14, wherein the fixation solution disinfects and preserves the tissue specimen.

16. The method of claim 14, wherein the staining solution includes at least one of hematoxylin and eosin.

17. The method of claim 14, wherein the optical clearing solution reduces optical scattering in the tissue specimen.

18. The method of claim 14 wherein applying an optical clearing solution to the tissue specimen comprises:
   monitoring at least one of light transmittance through the tissue specimen and absorbance at a region of the visible light spectrum in the tissue specimen.

19. An optical imaging method, comprising:
   introducing a thin-needle core biopsy (TNCB) biological tissue specimen into a microfluidics device;

washing the TNCB biological tissue specimen in the microfluidics device while preserving an elongated shape of the TNCB biological tissue specimen;

fixing the TNCB biological tissue specimen in the microfluidics device while preserving the elongated shape of the TNCB biological tissue specimen;

staining the TNCB biological tissue specimen in the microfluidics device while preserving the elongated shape of the TNCB biological tissue specimen;

clearing the TNCB biological tissue specimen in the microfluidics device while preserving the elongated shape of the TNCB biological tissue specimen;

adding a contrast agent to the TNCB biological tissue specimen in the microfluidics device while preserving the elongated shape of the TNCB biological tissue specimen; and optically imaging at least a portion of the TNCB biological tissue specimen, wherein the microfluidics device is structured to preserve the elongated shape of the TNCB biological tissue specimen during the washing, fixing, staining, clearing, adding, and optical imaging.

20. The method of claim 19, comprising:
applying embedding media to the biological tissue specimen prior to optically imaging at least the portion of the biological tissue specimen.

21. The method of claim 19, wherein staining the biological tissue specimen includes at least one of applying an absorptive dye to the biological tissue specimen and applying a fluorescence marker to the biological tissue specimen.

22. The method of claim 19, wherein preserving the elongated shape of the biological tissue specimen includes advancing the biological tissue specimen within the microfluidics device using at least one of compressive pressure and vacuum pressure.

23. The method of claim 19, wherein the acts of washing, fixing, staining, clearing, and adding the contrast agent include the act of passing a respective fluid through at least one interface in the microfluidics device.

24. The method of claim 19, wherein the act of optically imaging at least the portion of the biological tissue specimen includes passing light through at least one substantially transparent facet of the microfluidics device.

* * * * *

UNITED STATES PATENT AND TRADEMARK OFFICE
CERTIFICATE OF CORRECTION

PATENT NO. : 10,557,778 B2
APPLICATION NO. : 14/453938
DATED : February 11, 2020
INVENTOR(S) : Eric J. Seibel et al.

Page 1 of 1

It is certified that error appears in the above-identified patent and that said Letters Patent is hereby corrected as shown below:

On the Title Page

Column 2, Other Publications, Line 22 the reference beginning with "Botcherby et 31.:":
"16(26:21843-21848" should read, --16(26):21843-21848--.

Signed and Sealed this
Twentieth Day of October, 2020

Andrei Iancu
*Director of the United States Patent and Trademark Office*